US011564770B2

United States Patent
Serra et al.

(10) Patent No.: US 11,564,770 B2
(45) Date of Patent: Jan. 31, 2023

(54) SURGICAL SYSTEMS

(71) Applicant: NuVasive, Inc., San Diego, CA (US)

(72) Inventors: Michael Serra, San Diego, CA (US);
Thomas Sweeney, San Diego, CA (US); Jeremy Winston, San Diego, CA (US); Ellie Perry, San Diego, CA (US); Steven Lillig, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 17/407,075

(22) Filed: Aug. 19, 2021

(65) Prior Publication Data

US 2022/0061955 A1 Mar. 3, 2022

Related U.S. Application Data

(60) Provisional application No. 63/073,902, filed on Sep. 2, 2020.

(51) Int. Cl.
*A61B 90/50* (2016.01)
*A61B 17/34* (2006.01)
*A61B 17/00* (2006.01)

(52) U.S. Cl.
CPC .......... *A61B 90/50* (2016.02); *A61B 17/3423* (2013.01); *A61B 2017/00477* (2013.01)

(58) Field of Classification Search
CPC ................ A61B 90/50; A61B 17/3423; A61B 2017/00477; A61B 17/3421; A61B 2090/508
See application file for complete search history.

(56) References Cited

U.S. PATENT DOCUMENTS

| | | | |
|---|---|---|---|
| 3,221,743 A | 12/1965 | Thompson | |
| 5,555,897 A | 9/1996 | Lathrop, Jr. et al. | |
| 6,213,671 B1 | 4/2001 | Chang | |
| 6,264,396 B1 * | 7/2001 | Dobrovolny | A61B 17/0206 403/384 |
| 6,277,094 B1 | 8/2001 | Schendel | |
| 6,520,907 B1 | 2/2003 | Foley et al. | |
| 6,804,581 B2 | 10/2004 | Wang | |
| 7,124,755 B2 | 10/2006 | Van Hooser | |

(Continued)

OTHER PUBLICATIONS

International Search Report and Written Opinion dated Nov. 2, 2021 for International Application No. PCT/US2021/046776.

(Continued)

*Primary Examiner* — Richard G Louis
(74) *Attorney, Agent, or Firm* — Seager, Tufte & Wickhem LLP

(57) ABSTRACT

Systems, assemblies, devices, and methods for positioning surgical devices at surgical sites are disclosed. An adjustment assembly may include a first connector configured to connect to a surgical articulating arm and a second connector configured to connect to a tool, such as a surgical access tube. A joint assembly may be coupled to the first connector and an elongated assembly may be coupled to the joint assembly and the second connector. An actuator may be coupled to the joint assembly and may be adjusted to secure the elongated assembly in a desired position. One or more clips may be utilized with a surgical access tube to secure a surgical tool within a surgical access tube. The clip may have a single port or more than one port.

19 Claims, 27 Drawing Sheets

(56) References Cited

U.S. PATENT DOCUMENTS

| | | |
|---|---|---|
| 7,749,163 B2 | 7/2010 | Mulac |
| 8,360,971 B2 | 1/2013 | Farley |
| 8,425,404 B2 | 4/2013 | Wilson |
| 8,617,064 B2 | 12/2013 | Farley |
| 8,696,562 B2 * | 4/2014 | Mulac .................... A61B 17/02 600/227 |
| 8,795,167 B2 | 8/2014 | Ainsworth |
| 9,320,506 B2 | 4/2016 | Bertagnoli |
| 9,561,059 B1 | 2/2017 | Tohmeh |
| 10,517,692 B2 | 12/2019 | Eyre |
| 10,786,330 B2 | 9/2020 | Chegini |
| 10,806,328 B2 | 10/2020 | Koteles |
| 10,835,345 B2 | 11/2020 | Billard |
| 2003/0208187 A1 | 11/2003 | Layer |
| 2008/0047064 A1 | 2/2008 | Theran |
| 2011/0130793 A1 | 6/2011 | Woolley |
| 2014/0296650 A1 | 10/2014 | Weisshaupt |
| 2016/0310293 A1 | 10/2016 | Abdou |
| 2017/0014117 A1 * | 1/2017 | Capote ................... A61B 90/57 |
| 2019/0365489 A1 * | 12/2019 | Kasai ................. A61B 1/00188 |
| 2020/0085530 A1 | 3/2020 | Sauer |
| 2020/0179056 A1 | 6/2020 | Ando et al. |
| 2020/0237207 A1 | 6/2020 | Pimenta et al. |
| 2020/0367873 A1 | 11/2020 | Troxell et al. |
| 2021/0137511 A1 | 5/2021 | Garcia-Bengochea |
| 2021/0236107 A1 | 8/2021 | Serowski |

OTHER PUBLICATIONS

Depuy Synthes, Insight Tubes Surgical Technique (2017).
Medtronic, METRx Surgical Technique (2009).
Spinal Elements, Lucent MIS TLIF Posterior Access (2017).
Stryker, LITe Decompression System Surgical Technique (2016).
Zimmer, Viewline Tube Retraction System Reference Guide (2013).

* cited by examiner

SURGICAL SYSTEMS

CROSS-REFERENCE TO RELATED APPLICATIONS

This application claims priority to U.S. Provisional Application No. 63/073,902, filed Sep. 2, 2020, and titled SURGICAL SYSTEMS, which is hereby incorporated by reference in its entirety for any and all purposes.

BACKGROUND

A wide variety of surgical medical devices and systems have been developed for a variety of uses. Some of these devices and systems include surgical tools, implants, articulating arms, surgical end effectors, and the like. These devices and systems are manufactured by any one of a variety of different manufacturing methods and may be used according to any one of a variety of methods. Of the known surgical medical devices, systems, and methods, each has certain advantages and disadvantages.

BRIEF SUMMARY

This disclosure provides design, material, manufacturing method, and use alternatives for surgical medical devices and systems. An example assembly may include, a first connector configured to connect to a surgical articulating arm, a second connector configured to connect to a surgical tool, a joint assembly coupled to the first connector, an elongated assembly coupled to the second connector, and an actuator coupled to the joint assembly. The joint assembly may be configured to receive the elongated assembly and the actuator is configured to adjust to fix the elongated assembly at a location with respect to the joint assembly and adjust to release the elongated assembly from the location.

Alternatively or additionally to any of the embodiments in this section, the second connector is configured to adjust relative to the elongated assembly.

Alternatively or additionally to any of the embodiments in this section, the elongated assembly is configured to adjust to fix the second connector at a position with respect to the elongated assembly and adjust to release the second connector from the position.

Alternatively or additionally to any of the embodiments in this section, the second connector comprises a channel configured to receive the surgical tool when connecting the surgical tool to the second connector.

Alternatively or additionally to any of the embodiments in this section, the elongated assembly is adjustable relative to the first connector.

Alternatively or additionally to any of the embodiments in this section, the joint assembly comprises a housing and a rotational joint configured to couple to the elongated assembly, wherein the rotational joint is configurated to rotationally adjust with in the housing.

Alternatively or additionally to any of the embodiments in this section, the rotational joint comprises a ball joint.

Alternatively or additionally to any of the embodiments in this section, the actuator has a first position with respect to the joint assembly in which the joint assembly is unlocked and the elongated assembly is translatable relative to the joint assembly, and the actuator has a second position with respect to the joint assembly in which the elongated assembly is fixed with respect to the joint assembly.

Alternatively or additionally to any of the embodiments in this section, wherein the joint assembly comprises a housing and a rotatable joint configured to receive the elongated assembly and rotate relative to the housing, and when the actuator is in the first position, the rotatable joint and the elongated assembly are configured to rotate about two or more axes.

Alternatively or additionally to any of the embodiments in this section, the actuator is configured to cause the rotatable joint to be compressively fixed relative to the housing when the actuator is in the second position.

Alternatively or additionally to any of the embodiments in this section, the actuator is configured to cause the elongated assembly to be compressively fixed relative to the housing when the actuator is in the second position.

In a further example, a system may include an adjustment assembly having a first end configured to connect to an articulating arm and a second end, a surgical access tube configured to connect to the second end of the adjustment assembly, and the adjustment assembly may be configured to facilitate adjusting the surgical access tube with respect to the articulating arm irrespective of adjusting the articulating arm.

Alternatively or additionally to any of the embodiments in this section, the adjustment assembly may include an elongated assembly, a first connector at the first end, wherein the first connector is configured to be coupled to the elongated assembly using a joint assembly, and a second connector at the second end, wherein the second connector is configured to connect to the surgical access tube.

Alternatively or additionally to any of the embodiments in this section, the surgical access tube is configured to rotate about two or more axes when the surgical access tube is connected to the adjustment assembly.

Alternatively or additionally to any of the embodiments in this section, the system may further comprising an instrument clip configured to be received within the surgical access tube and connect to the surgical access tube.

Alternatively or additionally to any of the embodiments in this section, the instrument clip is configured to engage a top edge of the surgical access tube to secure an instrument at a position between the instrument clip and the surgical access tube.

Alternatively or additionally to any of the embodiments in this section, the instrument clip is configured to be rotated when in the surgical access tube.

In a further example, a method may include connecting a surgical access tube to an adjustment assembly for coupling to an articulating arm, adjusting the surgical access tube to a surgical position, securing the surgical access tube in the surgical position, and securing an instrument at a location with respect to the surgical access tube by inserting an instrument clip into a tube of the surgical access tube, and wherein securing the adjustment assembly in the surgical position and securing the instrument at the location with respect to the surgical access tube facilitates positioning the surgical access tube at a surgical site.

Alternatively or additionally to any of the embodiments in this section, inserting the instrument clip into the tube includes positioning a port of the instrument clip around the instrument inserted into the tube.

Alternatively or additionally to any of the embodiments in this section, the method may further comprise adjusting the surgical access tube to a surgical position includes adjusting the adjustment assembly about a first axis, a second axis, and a third axis, and the first axis and the second axis are associated with a joint assembly coupled to a first connector of the adjustment assembly for coupling to the articulating arm and the third axis is associated with a second connector of the adjustment assembly for connecting to the surgical access tube.

In a further example, an apparatus may include a body, a first wing extending radially outward from the body, a second wing extending radially outward from the body, and one or more ports, and wherein the first wing and the second wing are configured to rest on a tube of a surgical access tube assembly and the body is configured to be positioned within the tube when the first wing and the second wing are resting on the tube.

Alternatively or additionally to any of the embodiments in this section, the body, the first wing, the second wing, and the one or more ports are unitarily formed.

Alternatively or additionally to any of the embodiments in this section, the body applies a radially outward force on an inner surface of the tube when the first wing and the second wing are resting on the tube.

Alternatively or additionally to any of the embodiments in this section, the one or more ports define a space between an outer surface of the body and an inner surface the tube configured to receive a surgical tool.

Alternatively or additionally to any of the embodiments in this section, wherein the body is configured to flex inward in response to radially inward forces applied to the first wing and the second wing.

Alternatively or additionally to any of the embodiments in this section, the one or more ports comprise a first port and a second port.

Alternatively or additionally to any of the embodiments in this section, the first wing and the second wing are configured to rest on a top edge of the tube.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
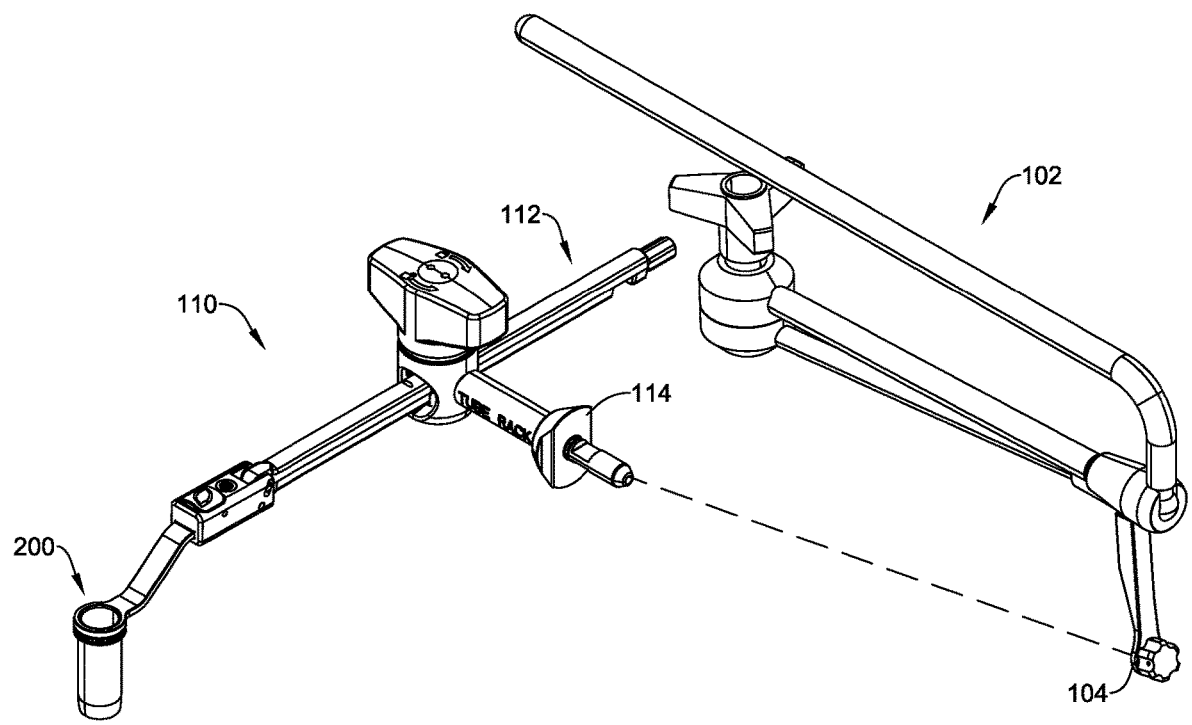
FIG. 1 is schematic perspective view of an illustrative surgical system for use with an articulating arm.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

A number of medical procedures, such as spinal surgeries and other suitable procedures, utilize surgical access systems and associated devices and instrumentation. Surgical access systems may include or be attachable to an articulating arm (e.g., a manually articulating arm or a robotic articulating arm) to facilitate locating the surgical access systems at a surgical site. However, existing articulating arms may have limited ranges of movement or may be bulky and make it difficult to adjust surgical devices and instruments attached thereto to precise surgical site locations. Disclosed herein are connector assemblies and systems that can be used with various articulating arms that allow for relatively quick and efficient connection and adjustment of the devices and instruments to be attached to an articulating arm. In some cases, the articulating arm may facilitate large position adjustments of the devices and instruments used in a surgery and the connector assemblies configured to connect to articulating arms that are discussed herein may facilitate both large and small or precise position adjustments of the devices and instruments used in a surgery.

Further, once devices and instruments used in a surgery have been located at a surgery site, it may be desirable to use multiple surgical devices or instruments at the surgical site with the devices and instruments connected to the articulating arm and positioned surgical site. However, the use of multiple surgical devices or instruments may be limited by users' ability to hold the devices or instruments at the surgical site (e.g., ability to hold multiple devices, ability to hold devices steady, etc.) or space available for users and systems to secure device at the surgical site. Disclosed herein are components configured to engage or secure surgical devices and instruments to or relative to devices and instruments (e.g., surgical access tube assemblies, etc.) connected to an articulating arm and positioned at the surgical site. Such components may be configured to be unobtrusive to the use of the positioned devices and instruments connected to the articulating arm and other devices or instruments used therewith.

Turning to the Figures, FIG. 1 depicts a schematic perspective view of an illustrative surgical system 110 for use with an articulating arm 102. The articulating arm 102 may be any suitable type of articulating arm including, but not limited to, a manually adjustable articulating arm as depicted in FIG. 1, a robotic articulating arm, or other suitable articulating arm.

As depicted in FIG. 1, the surgical system 110 may include an adjustment assembly 112 and a surgical access tube assembly 200 configured for providing at least a portion of an operative corridor to a surgical site in a patient, among other suitable components, where the adjustment assembly 112 may allow for positioning the surgical access tube assembly 200 in a desired orientation or position relative to the surgical site. The adjustment assembly may facilitate adjusting the surgical access tube assembly 200 with respect to the articulating arm irrespective of adjusting the articulating arm. The adjustment assembly may provide adjustment in degrees of freedom beyond those provided by the articulating arm. Although not required, the surgical access tube assembly 200 may be configured to connect to an end of the adjustment assembly 112, as depicted in FIG. 1. The adjustment assembly can be configured to receive or otherwise be connected to other surgical devices, such as expandable retractors.

In use, the adjustment assembly 112 may provide a stable connection between the articulating arm 102 and the surgical access tube assembly 200. Further, the adjustment assembly 112 may provide a user (e.g., surgeon, technician, etc.) an ability to make precise adjustments to the orientation or position of the surgical access tube assembly 200. In one example, the adjustment assembly 112, the surgical access tube assembly 200, or both may be adjustable about two or more axes.

The surgical system 110 may be configured to connect to the articulating arm 102 in any suitable manner. In one example, an articulating arm connector 114 of the surgical system 110 may be configured to connect to a surgical system connector 104 of the articulating arm 102, but this is not required. The articulating arm connector 114 and the surgical system connector 104 may have mating connections of any suitable type that allow for connecting and disconnecting the surgical system 110 to and from the articulating arm 102. Example types of connections include, but are not limited to, threaded connections, keyed connections, friction fit connections, other suitable connection types, or suitable combinations thereof.

Figure 2:
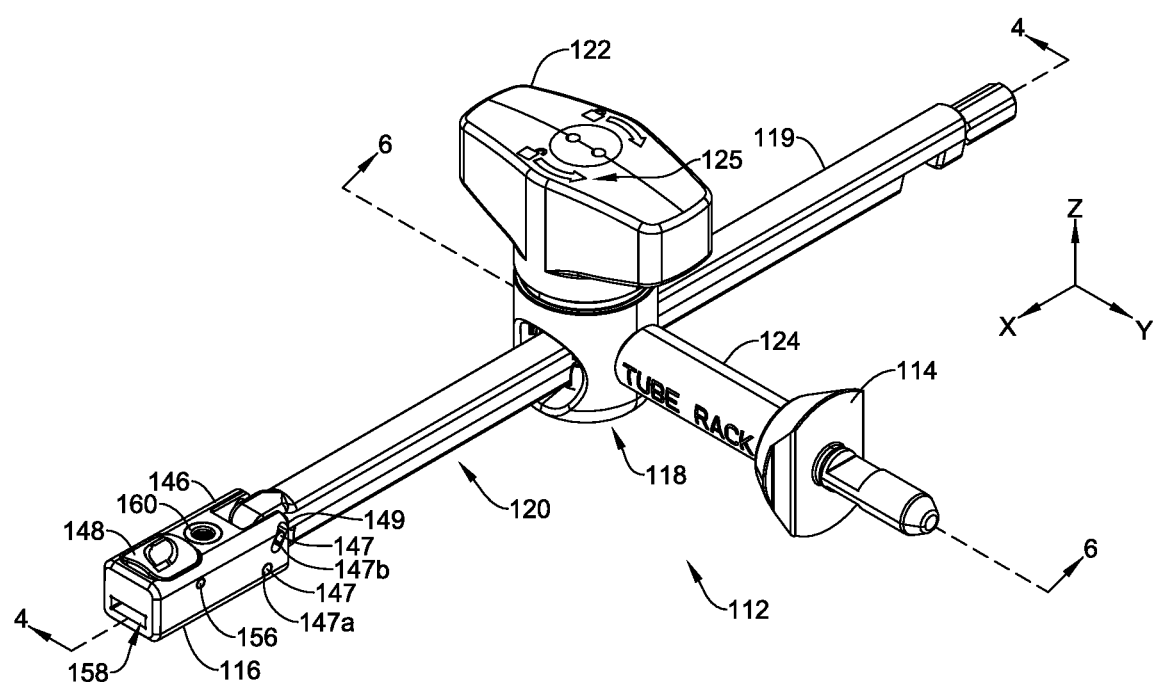
FIG. 2 is a schematic perspective view of an illustrative adjustment assembly.

FIG. 2 to depicts a schematic perspective view of the adjustment assembly 112 configured to facilitate stable and precise adjustment of surgical devices or components connected thereto and used therewith. Among other suitable components, the adjustment assembly 112 may include the articulating arm connector 114, surgical device connector 116, a joint assembly 118, an elongated assembly 120, an actuator 122, and a post 124.

In operation, the surgical device connector 116 may be coupled to the elongated assembly 120 and joint assembly 118 may be configured to receive the elongated assembly 120 therein or therethrough. When the joint assembly 118 has received the elongated assembly 120, the actuator 122 may be actuated or otherwise adjusted (e.g., to a first position) to fix the elongated assembly 120 at location with respect to joint assembly 118, as depicted in FIG. 2. Further, when the elongated assembly 120 is fixed at the location with respect to the joint assembly 118, the actuator 122 may be actuated or otherwise adjusted (e.g., to a second position) to release the elongated assembly 120 from being fixed at the location.

When the actuator 122 is in a released position or unlocked position, the elongated assembly 120 may be able to translate along an X-axis and rotate about two or more axes (e.g., rotate about the X, rotate about a Y-axis, and rotate about a Z-axis). Further, the surgical device connector 116 may be configured to rotate about the Y-axis (e.g., as discussed in more detail below) when the actuator 122 is in the released position or unlocked position. When the actuator 122 is in an engaged position or lock position, the elongated assembly 120 may be fixed at a position (e.g., at an X-axis, Y-axis, and Z-axis position) relative to the joint assembly 118. Further, when the actuator 122 is in the engaged position or the lock position, the surgical device connector 116 may be fixed at a rotational position (e.g., at an angle) about the Y-axis relative to the elongated assembly 120 and relative to the joint assembly 118.

As depicted in FIG. 2, the actuator 122 may be a knob that may be actuated by rotating the knob, but other configurations of the actuator 122 are contemplated. Further, although not required, the actuator 122 may include indicia 125 thereon that indicates which directional movement thereof (e.g., rotational directional movement) locks or unlocks the joint assembly 118. Alternative or additional indicia providing information may be provided.

The post 124 may be coupled to the joint assembly 118 and the articulating arm connector 114 in any suitable manner. Example couplings may include, but are not limited to, a threaded coupling, a quick connect coupling, a weld coupling, an adhesive coupled, other suitable couplings, or suitable combinations of coupling types. In one example, the post 124 may be coupled to the joint assembly 118 using a weld connection and the post 124 may be coupled to the articulating arm connector using a threaded connection, but other coupling or connection configurations are contemplated. In some cases, two or more of the post 124, components of the joint assembly 118, and the articulating arm connector 114 may be unitarily, integrally, or monolithically formed.

The surgical device connector 116 may connect to the elongated assembly 120 in any suitable manner. In one example, the surgical device connector 116 may connect to the elongated assembly 120 using one or more pins 147. As depicted in FIG. 2, first and second pins 147a, 147b may extend through a rack 119 of the elongated assembly 120. When connected, the surgical device connector 116 may be configured to adjust relative to the elongated assembly 120.

The surgical device connector 116 may include an opening or channel 158 for receiving the surgical device (e.g., a surgical access tube assembly 200 or other suitable surgical devices) and a button connector 148 or other suitable actuator that may be actuated to release or accept the surgical device in the channel 158. The channel 158 may have any suitable dimensions that facilitate receiving the surgical device.

When a surgical device is to be received in the surgical device connector 116, a set screw 160 may be at a location for receiving the surgical device and when the surgical device has been received in the surgical device connector 116, the set screw 160 may be adjusted to engage the received surgical device through a housing 146 of surgical device connector 116. The set screw 160, however, may be an additional connector relative to the button connector 148 that stabilizes a received surgical device, but may be omitted if an extra connector for engaging the surgical device with the surgical device connector 116 is not desired.

To facilitate adjusting the surgical device connector 116 relative to the elongated assembly 120, the surgical device connector 116 may include one or more elongated openings 149. As depicted in FIG. 2, the surgical device connector 116 may be configured to pivot about the first pin 147a while the second pin 147b slides within the elongated opening 149. However, other suitable adjustable connections between the surgical device connector 116 and the elongated assembly 120 are contemplated.

Figure 3:
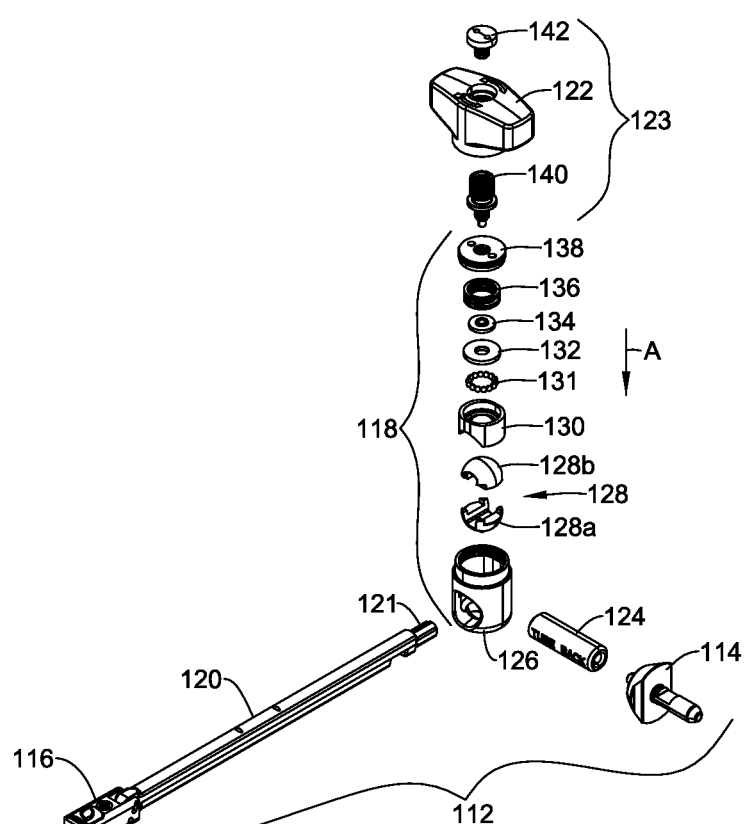
FIG. 3 is a schematic exploded view of the illustrative adjustment assembly depicted in FIG. 2.

FIG. 3 depicts an exploded view of the adjustment assembly 112 depicted in FIG. 2. Although depicted otherwise in FIG. 3, the actuator 122 may be part of the joint assembly 118.

As can be seen, the joint assembly 118 may comprise, among other additional or alternative components, a housing 126, a ball joint 128 (e.g., a rotational joint), a ball joint cap 130, a spacer or bearing assembly 131, a washer 132, a lock screw connector 134, a spring 136 (e.g., a wave spring or other suitable spring), and a housing cap 138 configured to engage the housing (e.g., via threaded connection or other suitable connection or coupling). The housing 126 may be configured to receive the ball joint 128, the ball joint cap 130, the washer 132, the lock screw connector 134, the spring 136, and the housing cap 138.

The actuator 122 may be configured to connect to or couple to the joint assembly 118 such that actuation of the actuator 122 may fix the joint assembly at a desired position or release the joint assembly 118 from the desired position. In one example configuration, the actuator 122 may be configured to be coupled to the joint assembly 118 via a lock screw 140, which may be inserted into or received at a bottom of the actuator 122 and an actuator screw 142 that may be inserted into or received at a top of the actuator 122. In some case, the actuator screw 142 may engage the lock screw 140 with a threaded connection to secure the actuator 122 to the lock screw 140, but this is not required and other suitable connection types may be utilized (e.g., a weld connection, adhesive connection, etc. between the lock screw 140 and the actuator 122). In some cases, the actuator 122, the lock screw 140, and the actuator screw 142, when included, may form an actuator assembly 123. Other suitable configurations of the actuator assembly 123 are contemplated.

The actuator assembly 123 may engage the joint assembly 118 in any suitable manner. In one example, the lock screw 140 may engage the housing cap 138 and extend through the lock screw connector 134. Although other coupling and connection configurations are contemplated, the lock screw 140 and the housing cap 138 may have a threaded connection. When so configured, rotation of the actuator 122 may result in a force (e.g., a compressive or other suitable force) acting on or releasing from the ball joint 128.

In operation, the lock screw 140 or other suitable component may engage or couple to the actuator 122 such that when the actuator 122 is adjusted (e.g., rotated or otherwise adjusted), the screw 140 may act on (e.g., apply a compression force to) the lock screw connector 134, the washer 132, the spacer or bearing assembly 131, the ball joint cap 130, the ball joint 128, or other suitable components of the joint assembly 118 such that a force in the direction of arrow A is applied to the joint assembly 118, which in turn causes the ball joint 128 and the elongated assembly 120 received therein to be frictionally or compressively fixed in a position relative to the housing 126. When the actuator 122 is released or adjusted (e.g., rotated further or back to a previous position), the force in the direction of arrow A acting on the housing cap 138, the spring 136, the ball joint cap 130, and the ball joint 128 may be reduced or released such that the ball joint 128 may move relative to the housing 126. To facilitate rotation of the ball joint 128 within the housing 126, an outer surface of the ball joint 128 may have a ball shape or may otherwise be rounded. Other suitable adjustable joints, configurations for joints, and actuator configurations may be utilized in addition to or as alternatives to using the ball joints 128, the configuration of the joint assembly 118 discussed herein, or the actuator assembly 123 discussed herein.

To facilitate compressively fixing the ball joint 128 at a position relative to the housing 126, an outer surface of the ball joint 128 may be treated or otherwise having markings thereon. Example surface treatments applied to the outer surface of the ball joint 128 to encourage a friction fit when the actuator 122 is actuated and allow the ball joint 128 to adjust (e.g., rotate) when the actuator 122 is not actuated or is released may include, but are not limited to, laser etching, laser ablation, chemical etching, vapor degreasing, blasting, etc. In one example, an outer surface of the ball joint 128 may be laser etched to facilitate frictionally fixing the ball joint 128 with respect to the housing 126.

The elongated assembly 120 may be received within the joint assembly 118. In one example, a handle 162 and an elongated portion of the elongated assembly 120 may be inserted into the housing 126 and through the ball joint 128. When inserted and when the joint assembly 118 is not fixed (e.g., the actuator 122 is not adjusted to a fixed or locked position), the elongated assembly 120 may be translatable within or otherwise relative to housing 126 and the ball joint 128 and configured to be rotationally positioned or adjusted with the ball joint 128 relative to the housing 126. When the joint assembly 118 is fixed, a clamping force (e.g., a compressive or clamping force) may be applied to the received elongated assembly 120 by the joint assembly 118 that may prevent any movement of a rack assembly thereof relative to the actuator 122 or the joint assembly 118.

Figure 4:
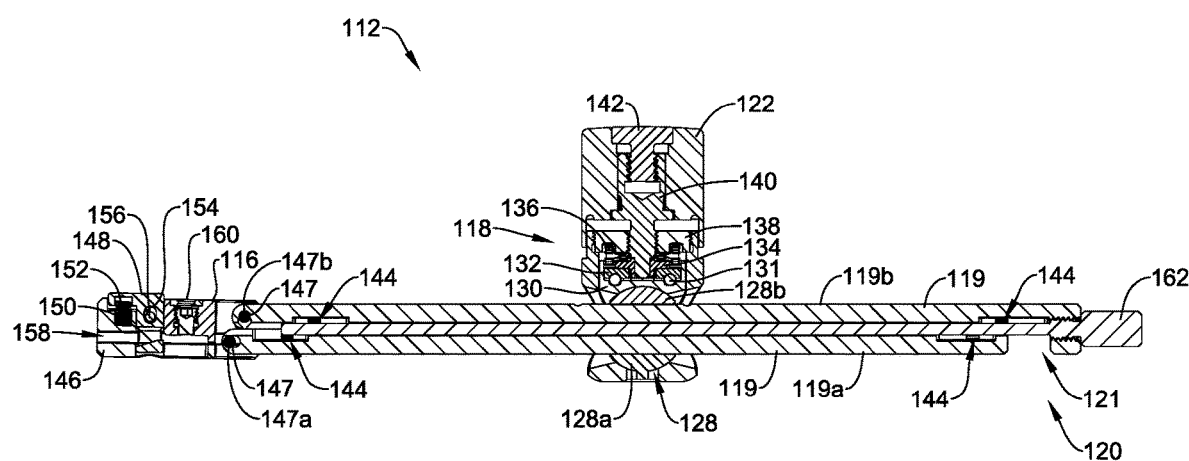
FIG. 4 is a schematic cross-sectional view of the illustrative adjustment assembly depicted in FIG. 2, taken along line 4-4.

FIG. 4 depicts a cross-sectional view of the adjustment assembly 112 taken along line 4-4 in FIG. 2. The actuator 122 coupled to the joint assembly 118 is in a position that causes the elongated assembly 120 to be fixed (e.g., a friction or compression force connection) at a location (e.g., translational or rotational location) with respect to the joint assembly 118. In some cases, the fixing of the elongated assembly 120 with respect to the joint assembly 118 may also fix the surgical device connector 116 at a position relative to the elongated assembly 120 by the joint assembly 118 applying a compression force to components of the elongated assembly 120 that facilitate adjusting a position of the surgical device connector. Further, the position of the actuator 122 may cause the joint assembly 118 and the elongated assembly 120 to be at a fixed position with respect to the actuator 122. The actuator 122 may be adjusted (e.g., rotated or otherwise adjusted in a suitable manner) to release the elongated assembly 120 relative to the joint assembly 118, release the surgical device connector 116 relative to the elongated assembly 12, release the elongated assembly 120 and the joint assembly 118 relative to the actuator 122, or release one or more other suitable components from a fixed position.

The elongated assembly 120 may take on any suitable configuration. In the example depicted in FIG. 4, the elongated assembly 120 may include a rack 119 and a shaft 121. The rack 119 may include a first rack 119a (e.g., a bottom rack) and a second rack 119b (e.g., a top rack). In some cases and although not required, the device connector 116 may be considered part of the elongated assembly 120.

The shaft 121, when included, may be configured to connect the first rack 119a and the second rack 119b to one another. In one example, the shaft 121 may extend through openings 144 (e.g., channels) of the first rack 119a and the second rack 119b, where the openings align along an axis to facilitate receiving the shaft 121. To secure the rack 119 and the shaft 121 to one another, the shaft 121 may include threads that are configured to engage threads of the first rack 119a, threads of the second rack 119b, or threads of the first rack 119a and the second rack 119b. In one example, as shown in FIG. 4, the threads may be located at an end portion of the second rack 119b. Further, the shaft 121 may include the handle 162 that a user may grasp to facilitate connecting or disconnecting the shaft 121 and the rack 119.

The rack 119 may be coupled to the housing 146 of the surgical device controller 116 in any suitable manner. Example connection or coupling types include, but are not limited to pin connections, screw connections, bolt and nut connections, other suitable connections, and combinations of connection types. As depicted in FIG. 4, the rack 119 may be coupled to the housing 146 of the surgical device connector 116 via one or more pins 147, where the first pin 147a may connect the first rack 119a to the housing 146 (e.g., via spaced apart openings in the housing 146) and the second pin 147b may connect the second rack 119b to the housing 146 (e.g., via the elongated openings 149, one of which is depicted in FIG. 2 and the other of which is located on an opposing wall of the housing 146). The second pin 147b may be configured to move within the elongated openings 149 based on a desired angulation of the surgical device connector 116 relative to the rack 119. Other configurations are contemplated.

The housing 146 of the surgical device connector 116 may include a channel 158 defining an opening for receiving a connector portion of a surgical device (e.g., the surgical access tube assembly 200 or other suitable surgical device) or other device. Further, the surgical device connector 116 may include the button connector 148 that extends through the housing 146 and the channel 158 such that an engagement component 150 (e.g., a ramped or tapered catch or other suitable engagement component) may be positioned or configured to engage the connector portion of a surgical device. In addition to or as an alternative to the button connector 148, other suitable connectors may be utilized to couple the surgical device to the surgical device connector 116.

The button connector 148 or other suitable connector may be coupled to the surgical device connector 116 in any suitable connecting or coupling manner discuss herein or otherwise. In one example, the button connector 148 may be coupled to the housing 146 via a pin 156 and may include an elongated opening or hole 154 that facilitates the button connector translating relative to the housing 146 to engage and disengage a surgical device received in the channel 158. In some cases, the button connector 148 may be biased to a connected position via a spring 152 to engage a received surgical device and the button connector 148 may be positioned in a disconnecting position (e.g., depressed) in response to a force acting thereon substantially opposite a biasing force of the spring 152 to receive the surgical device and release the received surgical device.

As discussed above with respect to FIG. 2, the surgical device connector 116 may include a set screw 160. The set screw 160, may be adjusted to engage or disengage a surgical device or other suitable device received in the channel 158. The set screw 160 may be configured to increase the stability of the connection between the surgical device connector 116 and the received surgical device over a stability that may be provided by the button connector 148, without another connector mechanism. Additional or alternative suitable connection features may be utilized to securely connect and disconnect the surgical device and the surgical device connector 116.

To facilitate positioning the surgical device connector 116 relative to the elongated assembly 120, the actuator 122 may be adjust to an unlocked position such that the first rack 119a and the second rack 119b may be adjusted relative to one another and an angle of surgical device connector 116 relative to the rack 119 may be adjusted by pivoting the housing 146 about the first pin 147a and sliding the second pin 147b in the slot or elongated opening 149 (e.g., as depicted in FIG. 2). Once the surgical device connector 116 is at a desired angle relative to the rack 119, the surgical device connector 116 may be fixed relative to the rack 119 by adjusting the actuator 122 to a locked position to fix the first rack 119a and the second rack 119b with respect to one another. Other configurations for facilitating positioning the surgical device connector 116 relative to the elongated assembly 120 and fixing the surgical device connector 116 at the relative position are contemplated.

Figure 5A:
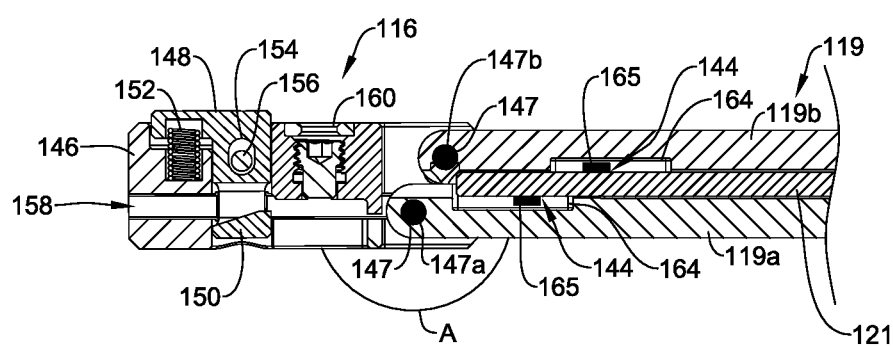
FIG. 5A is a schematic cross-sectional view depicting an illustrative connector of the adjustment assembly of FIG. 4 in a first position.
Figure 5B:
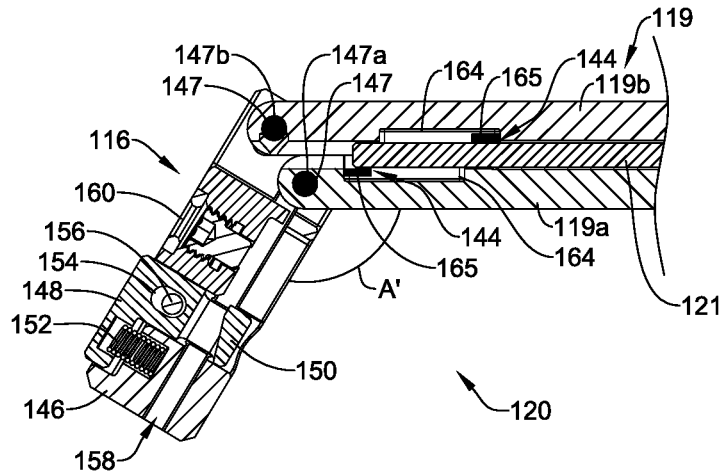
FIG. 5B is a schematic cross-sectional view depicting an illustrative connector of the adjustment assembly of FIG. 4 in a second position.

FIGS. 5A and 5B depict adjusting a position (e.g., an angle) of the surgical device connector 116 relative to the rack 119. FIG. 5A depicts the surgical device connector 116 at an angle A relative to the rack 119. FIG. 5B depicts the surgical device connector 116 at an angle A' relative to the rack 119, where angle A' is a smaller angle than angle A. Angle A and angle A' may be different relative angles with respect to one another or different absolute angles than what is depicted in FIGS. 5A and 5B.

FIG. 5A depicts the angle A at approximately one hundred eighty degrees. At this angle, the surgical device connector 116 is approximately parallel to the rack 119 in the X-axis. In such a configuration, the first rack 119a may be positioned beyond an end of the second rack 119b. FIG. 5B depicts the Angle A' at approximate one hundred twenty degrees. At this angle, the connector 116 is oblique to the rack 119 in the X-axis. In such a configuration the second rack 119b may be positioned beyond an end of the first rack 119a. In some cases, the first rack 119a and the second rack 119b may include spaces 164 configured to receive projections 165 of the other rack component that define the openings 144 configured to receive the shaft 121, where the spaces 164 may allow for those projections 165 to adjust as the first rack 119a and the second rack 119b adjust with respect to one another. In some cases, the spaces 164 of one of the first rack 119*a* and the second rack 119*b* may interact with projections 165 from the other of the first rack 119*a* and the second rack 119*b*, such that the spaces 164 and the projections 165 act as limits when adjusting the first rack 119*a* and the second rack 119*b* with respect to one another, but this is not required. Other configurations and other angles of angle A and angle A' are contemplated.

Figure 6:
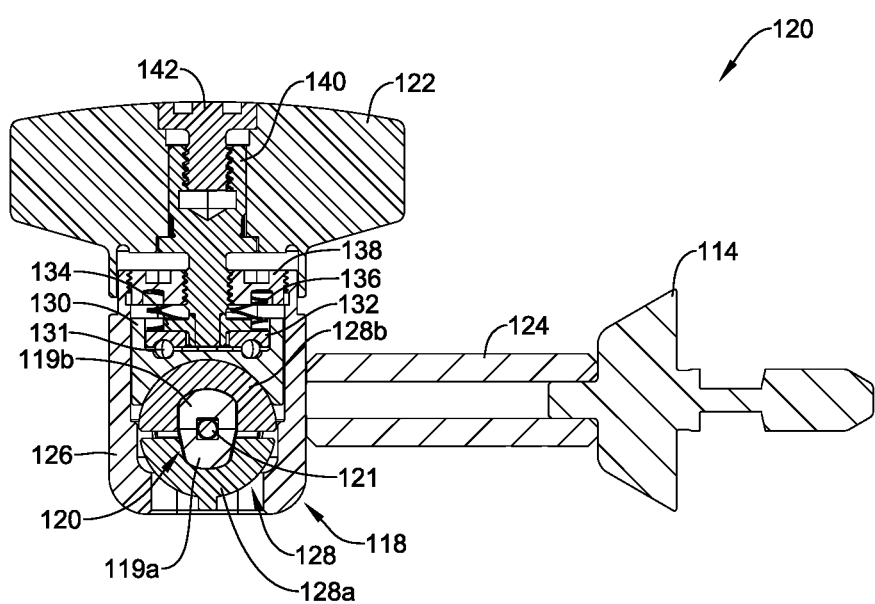
FIG. 6 is a schematic cross-sectional view of the illustrative adjustment assembly depicted in FIG. 2, taken along line 6-6.

FIG. 6 depicts a cross-sectional view of the adjustment assembly 112 taken along line 6-6 in FIG. 2. As depicted in FIG. 6, the articulating arm connector 114 may be inserted into the tube or post 124 extending from the joint assembly 118. Similar to the assembly 112 as depicted in FIG. 3, the shaft 121 is connecting the first rack 119*a* and the second rack 119*b* and the actuator 122 is positioned so as to fix the joint assembly 118 relative to the actuator 122 and cause the joint assembly 118 to apply a clamping force (e.g., a compressive force) to the elongated assembly 120 to secure the elongated assembly 120 at a translational location relative to the joint assembly 118.

Figure 7:
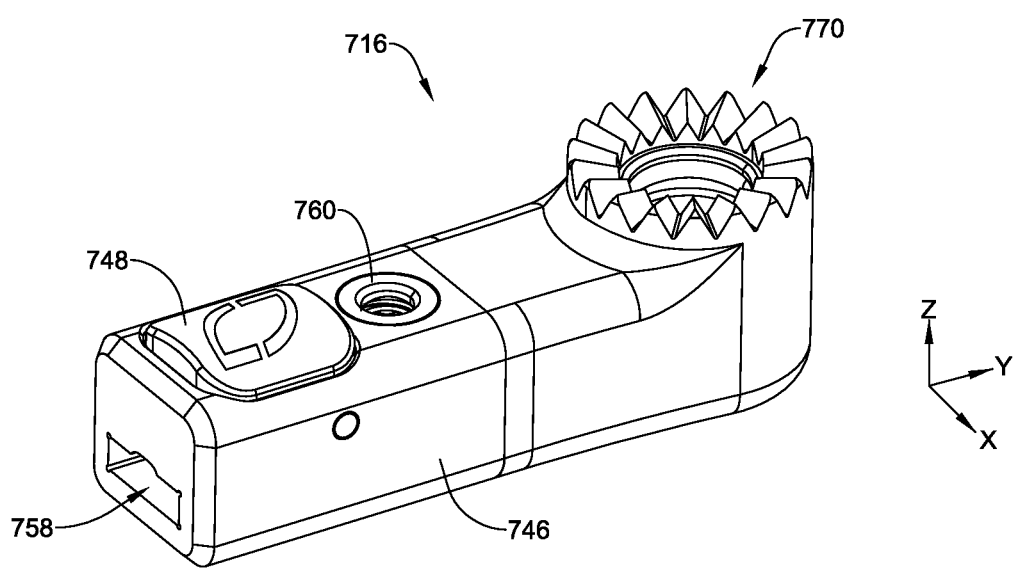
FIG. 7 is a schematic perspective view of an illustrative connector.

FIG. 7 depicts a perspective view of an illustrative surgical device connector 716. Although not necessarily required, the surgical device connector 716 may include, among other components, a housing 746, a button connector 748, an opening or channel 758, and a set screw 760. Although not required, the housing 746, the button connector 748, the opening or channel 758, and the set screw 760 may have features similar to and may be configured to operate similar to the housing 146, the button connector 148, the opening or channel 158, and the set screw 160 of the surgical device connector 716. Further, the surgical device connector 716 may include additional components that are similar in configuration and function to components of the surgical device connector 116 that facilitate receiving and connecting to a surgical device.

Further, the surgical device connector 716 may include a mating area 770. As depicted in FIG. 7, the mating area 770 may include teeth or other suitable mating structure configured to engage a surgical device connection area of an adapter or an articulating arm (e.g., an articulating arm similar to or different than the articulating arm 102). In some cases, the surgical device connector 716 may be rotated about the Z-axis relative to the adapter and the teeth or other suitable mating structure may facilitate maintaining the surgical device connector 716 at the desired rotational position relative to the adapter or articulating arm.

Figure 8:
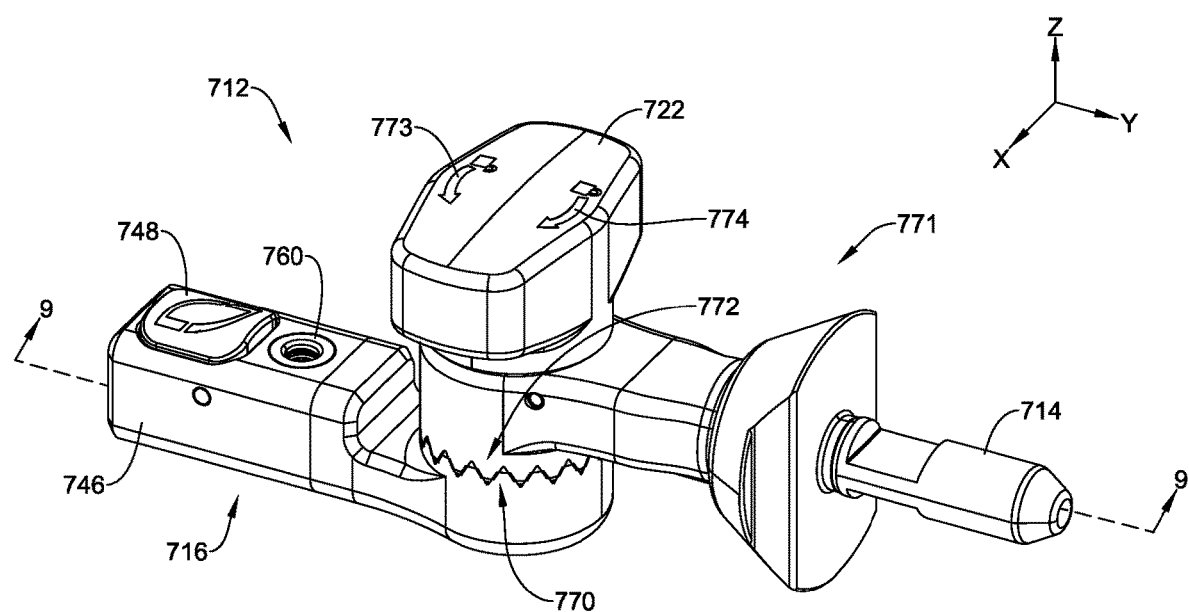
FIG. 8 is a schematic perspective view of an illustrative adjustment assembly including the connector of FIG. 7.

FIG. 8 depicts a perspective view of an adjustment assembly 712 including the surgical device connector 716 engaged with an adapter 771 configured to connect with an articulating arm. The adapter 771 may be configured to releasably engage surgical device connector 716 and engage an articulating arm via an articulating arm connector 714. The articulating arm connector 714 may have similar configurations and functions to the articulating arm connector 114, but this is not required.

The adapter 771 may include a mating area 772, which may be configured to mate with the mating area 770 of the surgical device connector 716. As depicted in FIG. 8, the mating area 772 may include teeth or other mating structure configured to mate with the teeth or other mating structure of the mating area 770 of the surgical device connector 716 and facilitate maintaining the surgical device connector 716 at a rotational position (e.g., about the Z-axis) relative the adapter 771.

The adapter 771 may include an actuator 722 configured to be actuated to secure the surgical device connector 716 and the adapter 771 at a position with respect to one another and release the surgical device connector 716 and the adapter 771 such that the relative position of the surgical device connector 716 and the adapter 771 may be adjusted about the Z-axis. In one example, the actuator 722 may be adjusted or actuated in a first direction represented by arrow 773 to facilitate allowing adjustment of the surgical device connector 716 with respect to the adapter 771 and adjusted or actuated in a second direction represented by arrow 774 to facilitate securing or locking the surgical device connector 716 and the adapter 771 at a position with respect to one another.

Figure 9:
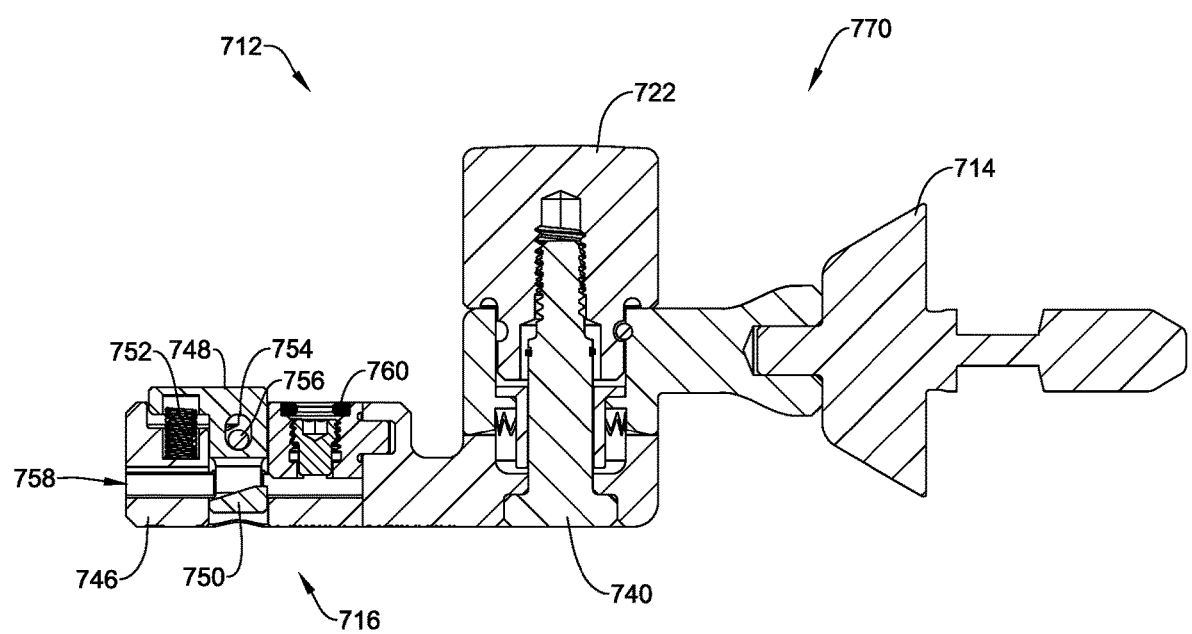
FIG. 9 is a schematic cross-sectional view of the adjustment assembly depicted in FIG. 8, taken along line 9-9.

FIG. 9 depicts a cross-sectional view of the adjustment assembly 712 taken along line 9-9 in FIG. 8. The depicted actuator 722 of the adapter 771 is in a position that causes the mating area 770 of the surgical device connector 716 to engage the mating area 772 of the adapter 771 to prevent rotational movement of the surgical device connector 716 relative to the adapter 771.

The adjustment assembly 712 may include a lock screw 740 that is configured to extend entirely or at least partially through the surgical device connector 716 and the adapter 771 to facilitate securing the surgical device connector 716 relative to the adapter 771. As depicted in FIG. 9, the lock screw 740 may extend through the surgical device connector 716 and the adapter 771, and engage the actuator 722. Although other couplings or connectors are contemplated, the lock screw 740 may engage the actuator 722 via a threaded connection. When so configured, rotation of the actuator 722 in the direction of arrow 773 (e.g., as depicted in FIG. 8) may allow for the adapter 771 and the surgical device connector 716 to translate along the Z-axis with respect to one another such that the mating areas 770, 772 separate from one another to allow the surgical device connector 716 and the adapter 771 to rotate about the Z-axis with one another. When the surgical device connector 716 and the adapter 771 are at a desired rotational position with respect to one another, rotation of the actuator 722 in the direction of arrow 774 (e.g., as depicted in FIG. 8) may cause the adapter 771 and the surgical device connector 716 to tighten along the Z-axis and the mating areas 770, 772 to engage one another to prevent rotational movement between the surgical device connector 716 and the adapter 771.

As discussed above with respect to FIG. 8, the surgical device connector 716 may have a similar configuration and function to the surgical device connector 116. For example, as depicted in FIG. 9, the surgical device connector 716 may have the housing 746, the button connector 748, an engagement component 750 of the button connector 748, a spring 752, an opening or hole 754 for receiving a pin 756, the opening or channel 758, and the set screw 760, which may be similar in configuration or function to components associated with reference numerals having a "1" in the hundreds place and similar numbers in the tens and ones places (e.g., 1##) associated with the surgical device connector 116.

Figure 10:
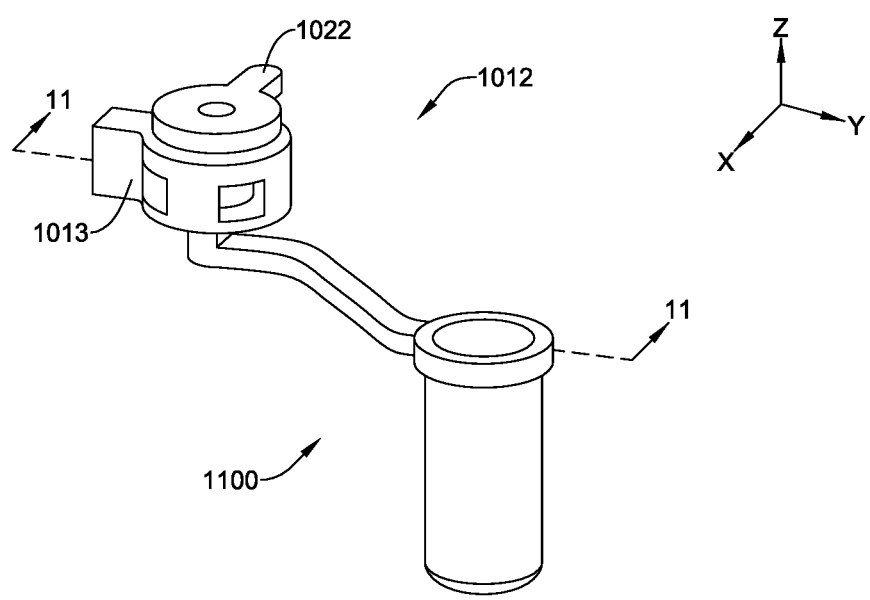
FIG. 10 is schematic perspective view of an illustrative surgical system for use with an articulating arm.

FIG. 10 depicts a perspective view of an illustrative adjustment assembly 1012 coupled to a surgical device (e.g., a surgical access tube assembly 1100). The adjustment assembly 1012 may be configured to engage with an articulating arm (e.g., the articulating arm 102 or other suitable articulating arm).

The adjustment assembly 1012 may include a housing 1013 and an actuator 1022. The actuator 1022 may be rotated about a Z-axis to facilitate receiving, engaging, and disengaging the surgical access tube assembly 1100. In some cases, the actuator 1022 may have a similar configuration as and may operate in a similar manner to the actuator 122 discussed above.

Figure 11:
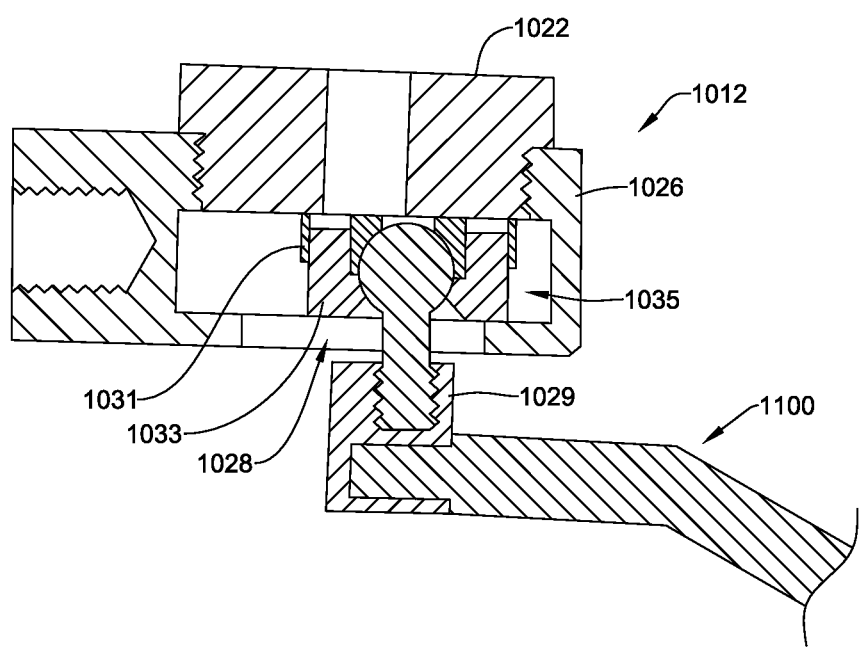
FIG. 11 is a schematic cross-sectional view of a portion of the surgical system depicted in FIG. 10, taken along line 11-11.

FIG. 11 illustrates a cross-sectional view taken along line 11-11 in FIG. 10 of the adjustment assembly 1012 coupled to the surgical access tube assembly 1100. As shown in FIG. 11, the adjustment assembly 1012 may comprise the actuator 1022, a housing 1026, a ball joint 1028, a connector 1029, a top cap 1031, a bottom cap 1033, and a channel 1035 in the housing 1026.

In one example of the adjustment assembly 1012, the actuator 1022 may be coupled to the housing 1026 via a threaded portion of the housing 1026, as depicted in FIG. 11. Other suitable connection or coupling techniques are contemplated. In a first mode of operation, rotation of the actuator 1022 from a first unlocked position to a second locked position may apply a compression to the top cap 1031. The compression force applied to the top cap 1031 may further apply a compression to the ball joint 1028. The compression force applied to the top cap 1031 may also result in applying a compression force to the bottom cap 1033. In the second locked position, the compression of the ball joint 1028 and the bottom cap 1033 may result in a clamping force that prevents any movement of the surgical access tube assembly 1100 or other suitably connected surgical device. In a second mode of operation, rotation of the actuator 1022 from the second locked position to the first unlocked position may remove the compression force applied to the top cap 1031, the ball joint 1028, and the bottom cap 1033. Removing the compression force applied to the top cap 1031, the ball joint 1028, and the bottom cap 1033, may enable the ball joint 1028 and the coupled surgical access tube assembly 1100 or other suitable surgical device to be moved in one or more directions (e.g., about two or more axes) within the channel 1035.

Figure 12:
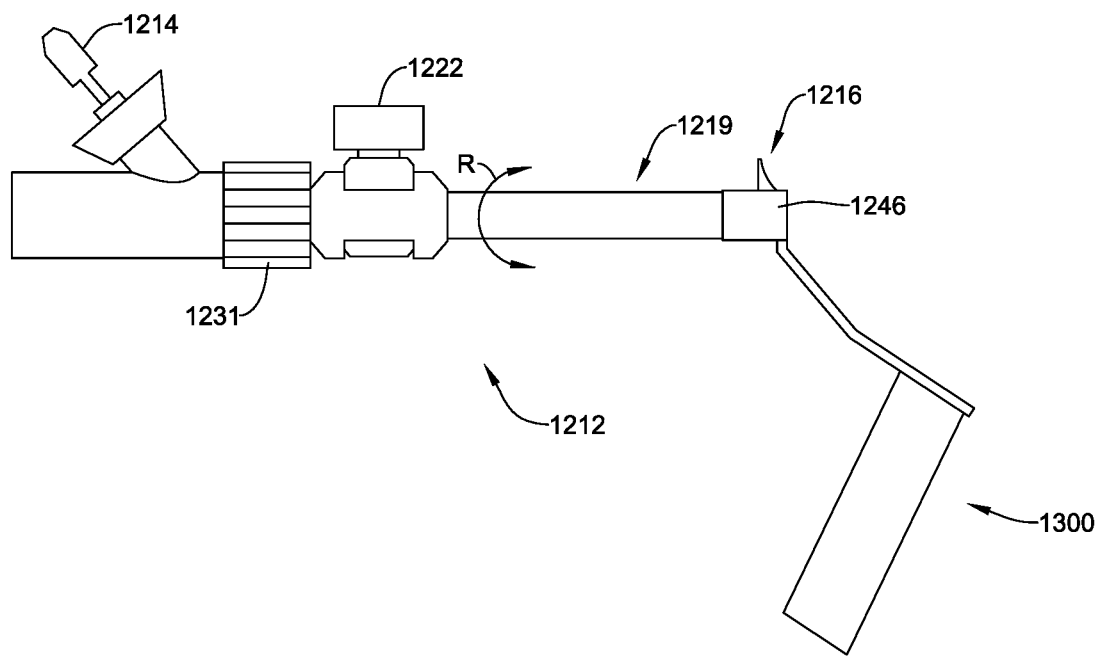
FIG. 12 is a schematic side view of an illustrative surgical system for use with an articulating arm.

FIG. 12 illustrates an example adjustment assembly 1212 and a surgical access tube assembly 1300 connected to the adjustment assembly 1212, where the adjustment assembly 1212 may be configured to connect to an articulating arm. The assembly 1212 may include a rack assembly 1219 that may be configured to work in a similar manner to the rack 119 discussed herein. The rack assembly 1219 may comprise or interact with a surgical device connector 1216 having a housing 1246. The housing 1246 may be configured to function in a manner similar to how the housing 146 functions to receive a surgical device or may function in additional or alternative suitable manners. The adjustment assembly 1212 may include a thumbwheel 1231 that is configured to control a rotation of the rack assembly 1219 in the directions of arrows R. The adjustment assembly 1212 may comprise an actuator 1222 (e.g., a lock knob) that may be configured to work in a similar manner as the actuator 122 or other actuators discussed herein. For example, rotation of the actuator 1222 to a locked position may produce a compression force that prevents the rack assembly 1219 and the housing 1246 of the surgical device connector 1216 from movement relative to an articulating arm connected to the adjustment assembly 1212. Rotation of the actuator 1022 from a locked position to an unlocked position relieves the compression force and thereby allows movement of the rack assembly 1219 and the housing 1246 relative to the articulating arm. The adjustment assembly 1212 may comprise a connector 1214 that may be configured to attach to an articulating arm in a manner similar to the connector 114.

Figure 13:
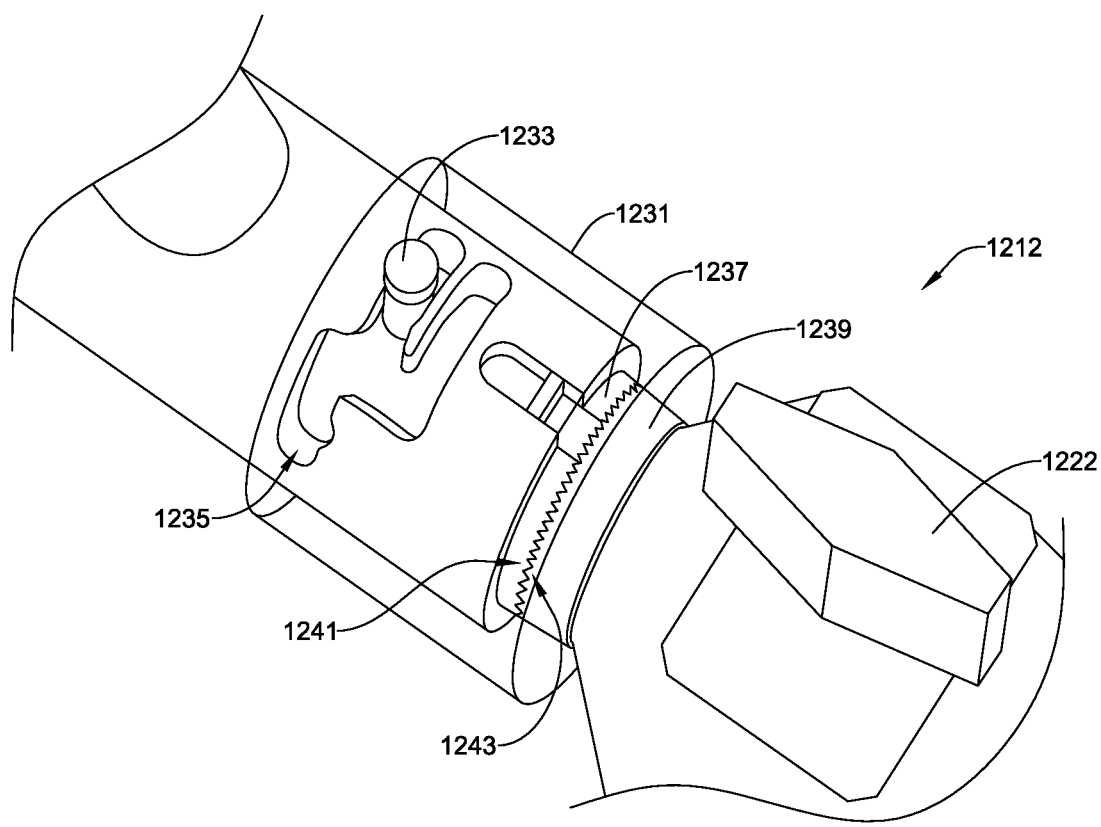
FIG. 13 is a schematic top view of a portion of the surgical system depicted in FIG. 12.

FIG. 13 is a partial view of the adjustment assembly 1212 depicted in FIG. 12, where the thumbwheel 1231 is shown in outline only to provide a view of other components of the adjustment assembly 1212. As shown in FIG. 13, the thumbwheel 1231 may be coupled to a pin 1233. The pin 1233 may be configured to move within a track 1235 based on rotation and translation of the thumbwheel 1231. The position of the pin 1233 may determine whether the rack assembly 1219 is in a first mode or second mode. In the first mode, the rack assembly 1219 cannot be rotated based on a coupling of a first linking member 1237 to a second linking member 1239. In a second mode, the pin 1233 may be moved to at least a second position (not shown) that decouples the first linking member 1237 from the second linking member 1239. In the second mode, rotation of the rack assembly 1219 may be possible based on a decoupling of the first linking member 1237 and the second linking member 1239.

Although not required, the first linking member 1237 and the second linking 1239 member may have mating areas. As depicted in FIG. 13, the first linking member 1237 may include a first mating area 1247 that includes teeth or other suitable mating structure configured to engage a second mating area 1249 of the second linking member 1239, which may have teeth or other suitable mating structure for engaging the first mating area 1247. In some cases, the mating areas or the teeth or other suitable mating structure thereof may facilitate maintaining the first linking member 1237 and the second linking member 1239 at a desired rotational position with respect to one another.

Figure 14:
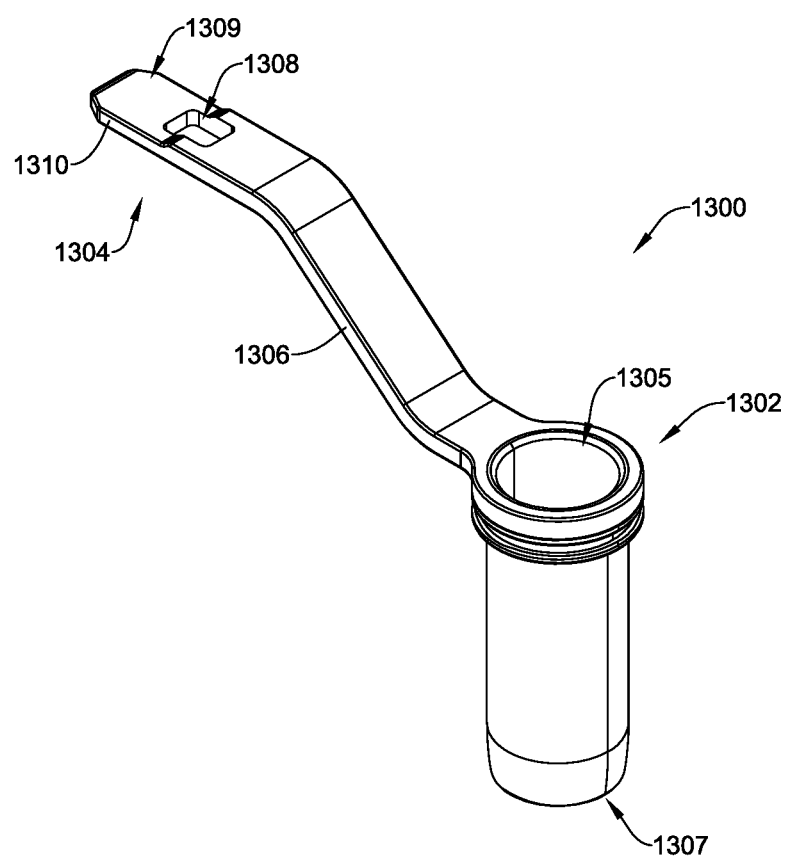
FIG. 14 is a schematic perspective view of an illustrative surgical access tube.
Figure 15:
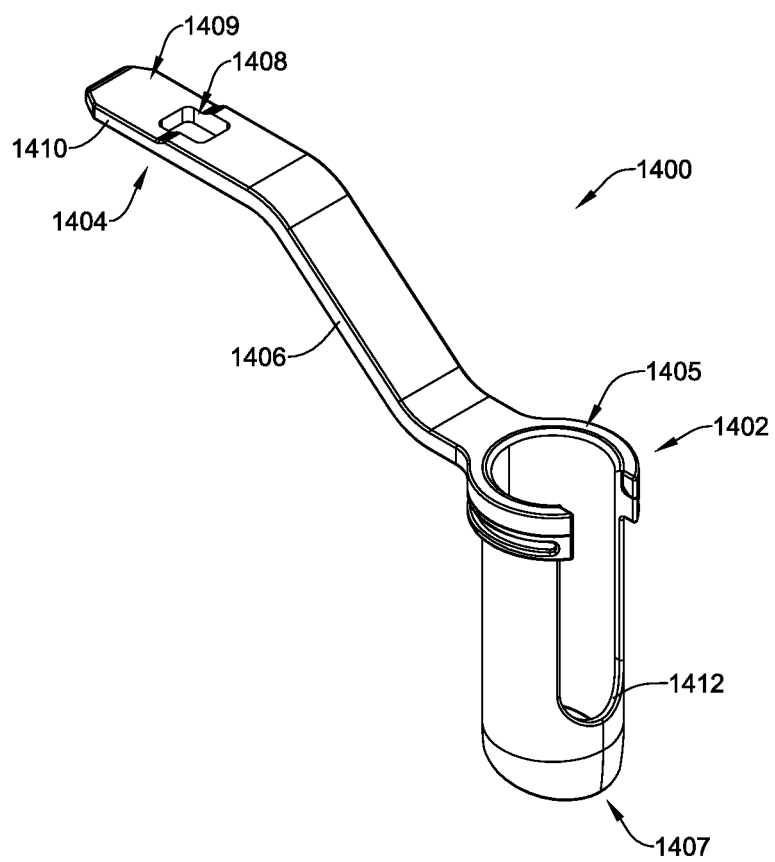
FIG. 15 is a schematic perspective view of an illustrative surgical access tube.

FIGS. 14 and 15 depict perspective views of surgical access tube assemblies 1300, 1400. The surgical access tube assemblies 1300, 1400 may be similar in configuration or function to the surgical access tube assembly 200 or the surgical access tube assembly 1100, but this is not required. Although other configurations are contemplated, the surgical access tube assemblies 1300, 1400 may include a tube 1302, 1402 for insertion into a subject (e.g., a patient or other suitable subject) at a surgical site, a connector portion 1304, 1404 and an arm portion 1306, 1406 connecting the tube 1302, 1402 and the connector portion 1304, 1404. As illustrated, the components of the surgical access tube assemblies 1300, 1400 are integral, unitary components. In other examples, the assemblies 1300, 1400 are formed from two or more separate components coupled together. The tube 1302 may be utilized for maintaining a surgical access site and providing space for a surgeon or other user to insert surgical devices (e.g., tools, blades, suction, lights, implants, etc.) into a surgical site. The tubes 1302, 1402 as illustrated are fixed structures. For instance, they are non-expandable (e.g., the diameter of the tube 1302 does not change).

The tube 1302, 1402 may take on any suitable configuration that facilitates reinsertion of surgical components into a surgical site. As depicted in FIG. 13, the tube 1302 may have a circular cross-sectional shape along its length with an opening at a top 1305 of the tube 1302 and an opening at a bottom 1307, but other suitable configurations are contemplated. As depicted in FIG. 14, the tube 1402 may have a generally circular cross-sectional shape along its length with an opening at a top 1405 of the tube 1402 and an opening at a bottom 1407 of the tube 1402. Further, the tube 1402 may include a cut-out portion 1412 that may extend through the wall of the tube 1402. The cut-out portion 1412 may facilitate insertion of a tool (e.g., a drill or other suitable tool) into a surgical site by providing space for receiving a handle or other suitable component of the tool. Alternatively or additionally, the cut-out portion 1412 may facilitate engaging one or more clips with the tube 1402. The tube 1302, 1402 may have any suitable dimensions configured to facilitate use at a surgical access site.

The connectors 1304, 1404 may have any suitable configuration configured to mate with surgical device connectors 116, 716, 1216 discussed herein or other suitable components for connecting a surgical access tube assembly to an articulating arm. As depicted in FIGS. 14 and 15, the connector 1304, 1404 may have an opening 1308, 1408 and a screw engaging portion 1309, 1409 defined by a tongue 1310, 1410 for engaging a connecting feature and a set screw, respectively, of a surgical device connector or adapter. In one example, the tongue 1310, 1410 of the connector 1304, 1404 may be configured to slide into a channel of the surgical device connectors 116, 716, 1216, connect with the connector 1029, or facilitate one or more other suitable connections or couplings.

Figure 16:
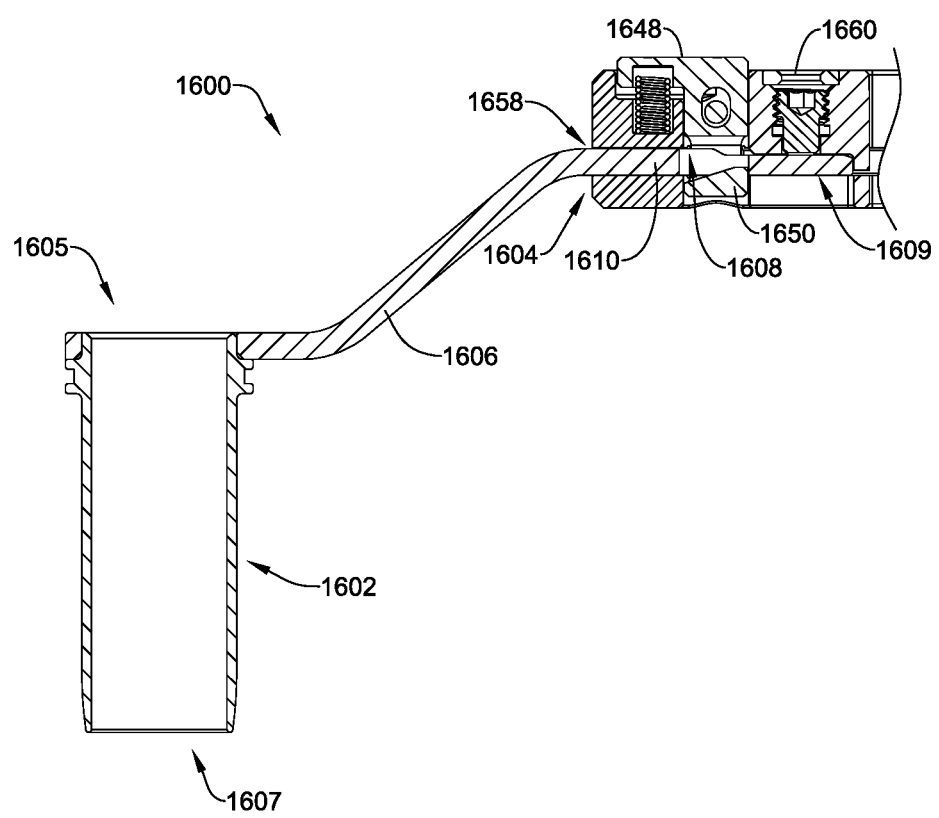
FIG. 16 is a schematic partial cross-sectional view of the surgical access tube depicted in FIG. 14 connected to the adjustment assembly depicted in FIG. 2.

FIG. 16 depicts a partial cross-sectional view of a surgical access tube assembly 1600 inserted into a surgical device connector 1616. The surgical access tube assembly 1600 may be similar to or different than the surgical access tube assemblies discussed herein. The surgical device connector 1616 may be similar to or different than the surgical device connectors discussed herein.

As depicted in FIG. 16, a tongue 1610 (e.g., a connector portion of the surgical device connector 1616) may be inserted into a channel 1658 of the surgical device connector 1616, such that an engagement component 1650 of a button connector 1648 engages the opening 1608 via a snap connection or other suitable coupling. Once the tongue 1610 is inserted into the channel 1658 and connected to the button connector 1648, a screw 1660 may be adjusted to apply a compression force on a screw engaging portion 1609 of the tongue 1610 to secure the surgical access tube assembly 1600 in a position with respect to the surgical device connector 1616. To release the surgical access tube assembly 1600 from the surgical device connector 1616, the set screw 1660 may be withdrawn from engagement with the screw engaging portion 1609 and the button connector 1648 may be depressed to release the opening 1608 from the engagement component 1650 of the button connector 1648.

Figure 17:
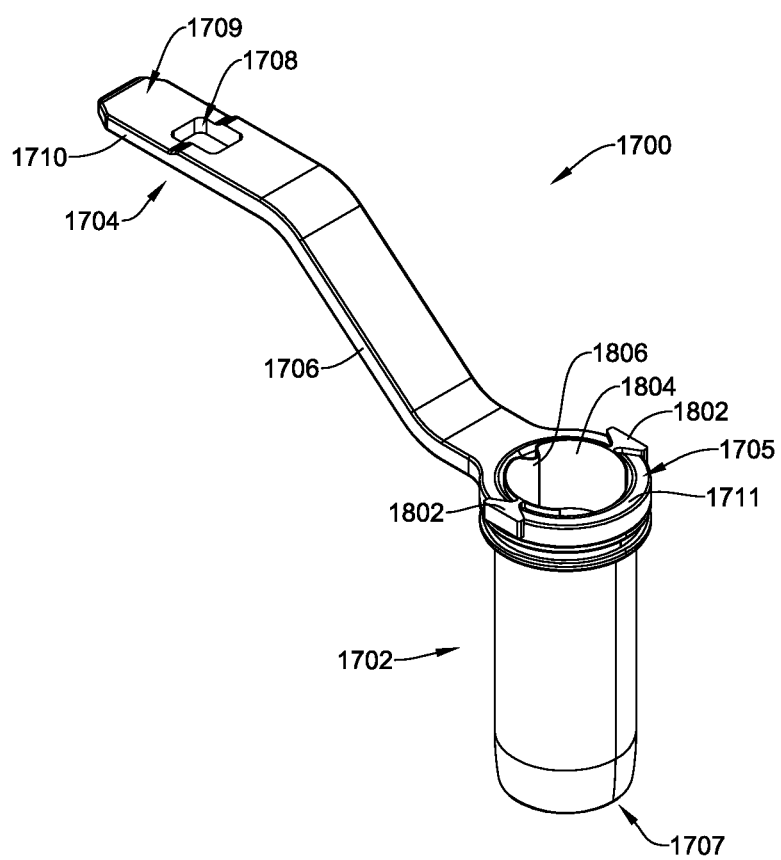
FIG. 17 is a schematic perspective view of an illustrative instrument clip received at a surgical access tube.

FIG. 17 depicts a perspective view of an illustrative surgical access tube assembly 1700, which may be similar to or different than the surgical access tube assemblies discussed herein, having a clip 1800 (e.g., an instrument clip) inserted in a tube 1702 for securing a surgical device (e.g., light, camera, suction tool, irrigation tool, retractor, other tools, or combinations thereof) between the clip 1800 and the tube 1702. Once inserted into the surgical access tube assembly 1700, the clip 1800 may be configured to be rotated therein. As depicted in FIG. 17, the surgical access tube assembly 1700 may include, among other features, the tube 1702, a connector 1704, an arm 1706, a top 1705 of the tube 1702, a bottom 1707 of the tube 1702, and a tongue 1710 defining an opening 1708 and a screw engaging portion 1709.

The clip 1800 may take on any suitable configuration for securing a surgical device at a location with respect to the surgical access tube assembly 1700, engaging the surgical access tube assembly 1700, and rotating the clip 1800 within the surgical access tube assembly 1700 and about a length of the clip 1800. As depicted in FIG. 17, the clip 1800 may have a generally rounded cross-section for inserting into the tube 1702 or other suitable configuration configured to fit within the tube 1702 and facilitating rotating the clip within the tube 1702. Further, the clip 1800 may include one or more wings 1802 for engaging an upper or top ledge or edge 1711 of the tube 1702 and which may extend beyond an outer circumference of the tube 1702. As depicted in FIG. 17, the clip 1800 may include two wings 1802 that may be generally opposed, which may facilitate placing the clip 1800 in the tube 1702, applying a radial pressure to the clip 1800, rotating or positioning the clip 1800 in the tube 1702, resisting the clip 1800 sliding too far toward the bottom 1707 of the tube 1702, and removing the clip 1800 from the tube 1702.

The clip 1800 may be formed from any suitable material. In some cases, the clip 1800 may be configured to be re-used in surgical settings, such as by being made of a biocompatible material that can be sanitized. In one example of such a configured clip 1800, the clip 1800 may be formed from 17-4 stainless steel. In some cases, the clip 1800 may be formed from a flexible material having a bias for biasing the clip 1800 outward (e.g., via a radially outward force) from a central axis. For example, when inserting the clip 1800 into the tube 1702, a user may apply an inward force (e.g., a radially inward force) against the one or more wings 1802 to reduce a diameter of a clip body 1804, insert the clip body 1804 into the tube 1702 such that the wings 1802 are resting on the upper ledge or edge 1711 of the tube 1702, and release the radially inward force on the wings 1802 such that the clip body 1804 may expand against an inner circumferential surface of the tube 1702. Alternatively, the clip 1800 may be formed from a non-biased material and the clip 1800 may be secured on the tube 1702 using only the wings 1802 without a radially outward bias force.

The clip 1800 may include one or more ports 1806. For example, the clip 1800 may include only one port, two ports, three ports, or more than three ports to the extent space allows for the additional ports. In the example of FIG. 17, the clip includes one port 1806. In some cases, the clip 1800 may include one or more ports extending exterior of the tube 1702 when the clip 1800 is connected to the surgical access tube assembly 1700.

The port 1806 may take on any suitable shape or configuration. As depicted in FIG. 17, the port 1806 may be an indent or a radially inward bend in the material of a clip body 1804 such that an instrument may be secured at the port 1806 between an outer surface of the clip body 1804 and an inner surface of a wall of the tube 1702. In some cases, a user may secure a surgical tool in the port 1806 between the clip 1800 and the tube 1702, while using other surgical devices in the remaining opening through the tube 1702 and the clip 1800.

The clip 1800 may have any suitable dimensions. In one example, the clip 1800 may be offered in a variety of diameters, lengths, or other suitable dimensions to facilitate using the clip 1800 with one or more differently configured tubes 1702 or surgical tools.

Figure 18:
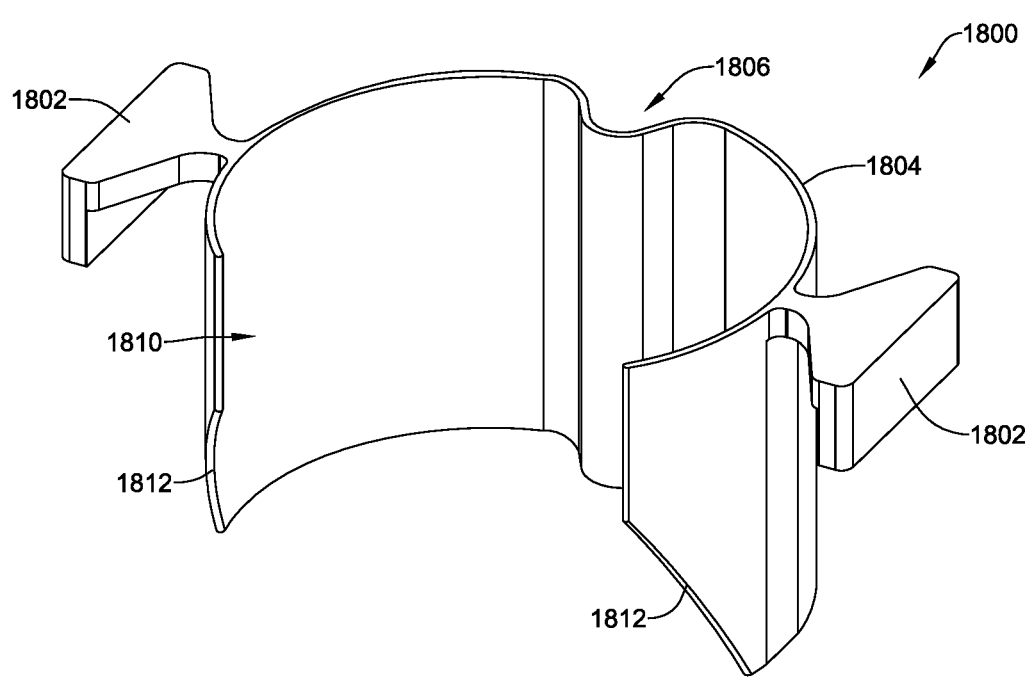
FIG. 18 is a schematic perspective view of an illustrative instrument clip.
Figure 19:
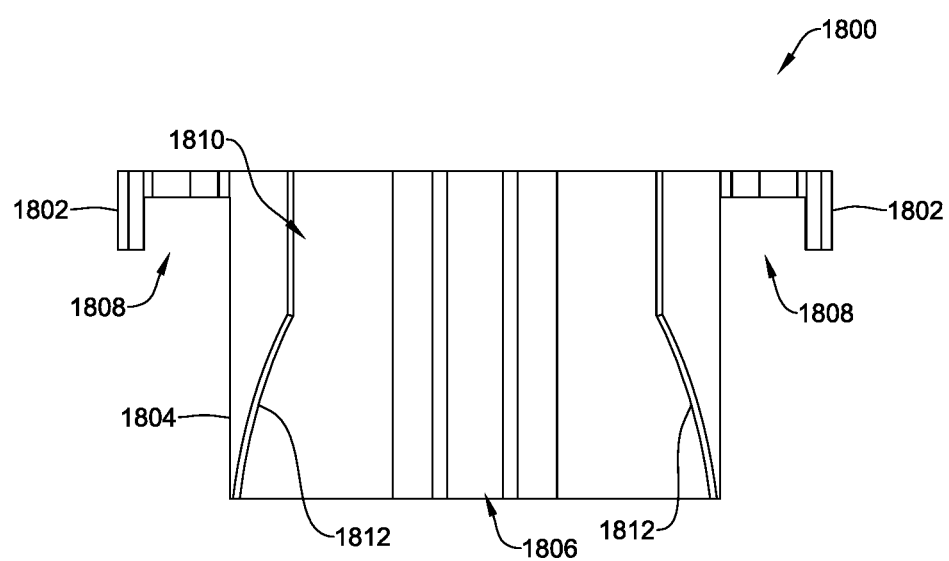
FIG. 19 is a schematic front view of the instrument clip depicted in FIG. 18.
Figure 20:
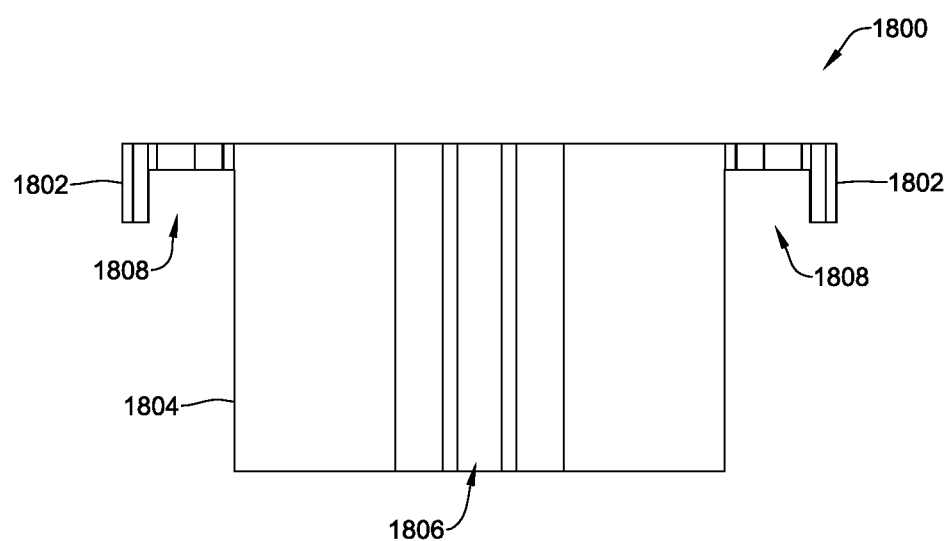
FIG. 20 is a schematic back view of the instrument clip depicted in FIG. 18.
Figure 21:
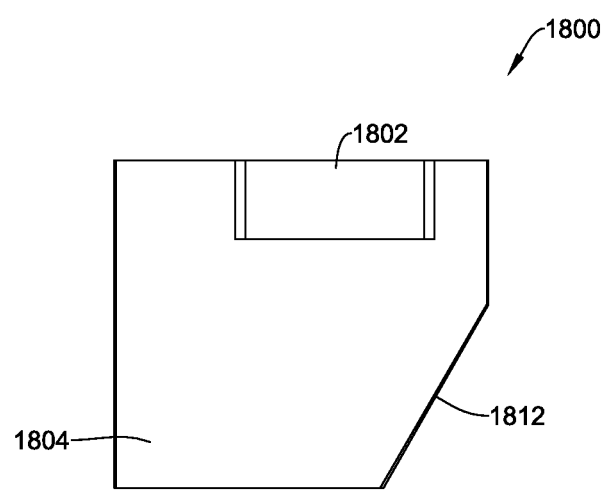
FIG. 21 is a schematic side view of the instrument clip depicted in FIG. 18.
Figure 22:
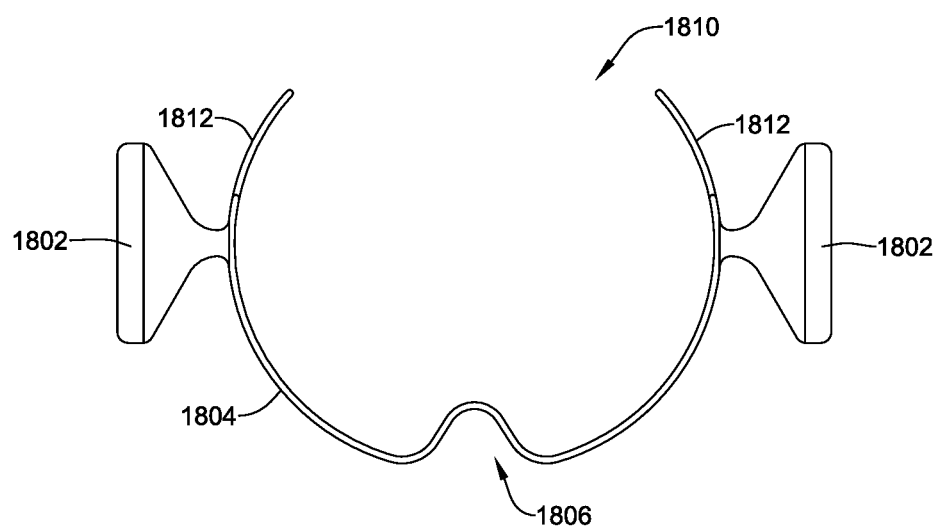
FIG. 22 is a schematic bottom view of the instrument clip depicted in FIG. 18.
Figure 23:
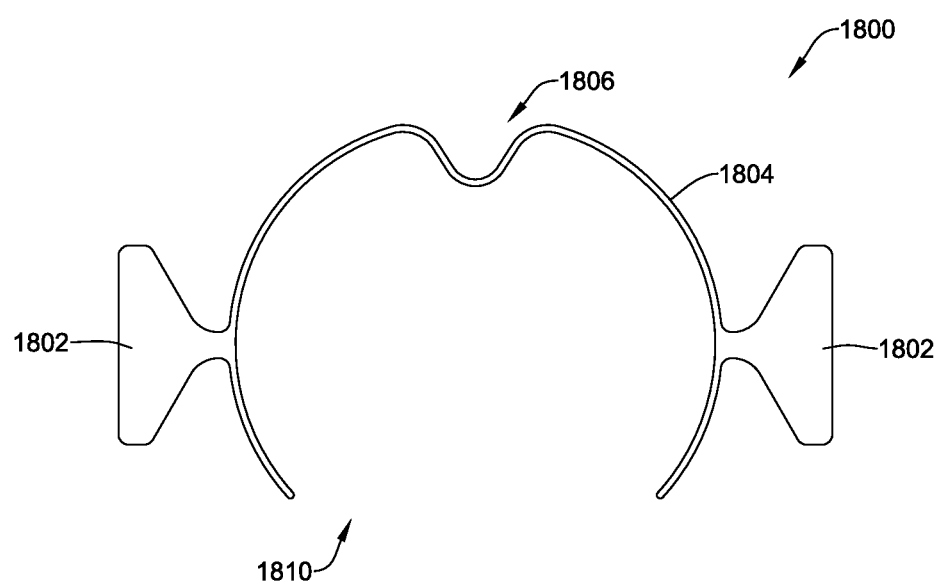
FIG. 23 is a schematic top view of the instrument clip depicted in FIG. 18.

FIGS. 18-23 depict various views of the clip 1800 having two wings 1802, the clip body 1804, and the port 1806. FIG. 18 depicts a perspective view of the clip 1800. FIG. 19 depicts a front view of the clip 1800. FIG. 20 depicts a back of the clip 1800. FIG. 21 depicts a side view of the clip 1800, where the left side view and the right side view of the clip 1800 may depict substantially the same features on opposite sides of the clip, but this is not required and the clip 1800 may have one or more left-right asymmetrical features. FIG. 22 is a bottom view of the clip 1800. FIG. 23 is a top view of the clip 1800.

The clip 1800, as depicted in FIGS. 18-23, may be a single component unitarily or monolithically formed from a single piece of material. This configuration, however, is not required and the clip 1800 may be formed from multiple components coupled together or multiple pieces of material.

The clip 1800, as depicted, may include the wings 1802 forming a generally U-shaped structure 1808 with the clip body 1804 for positioning the clip 1800 on the top edge of a surgical access tube assembly. Further, the clip 1800 may include an opening 1810 through a wall of the clip body 1804 to facilitate inserting the clip body 1804 into the surgical access tube assembly by radially compressing the clip 1800. In some cases, the clip 1800 may have tapered bottom edges 1812 at least partially defining the opening 1810. The tapered bottom edges 1812 may facilitate inserting the clip 1800 into the surgical tube in view of the reduced profile relative to straight edges, inserting and removing tools through the clip 1800, or other uses of the clip 1800.

Figure 24:
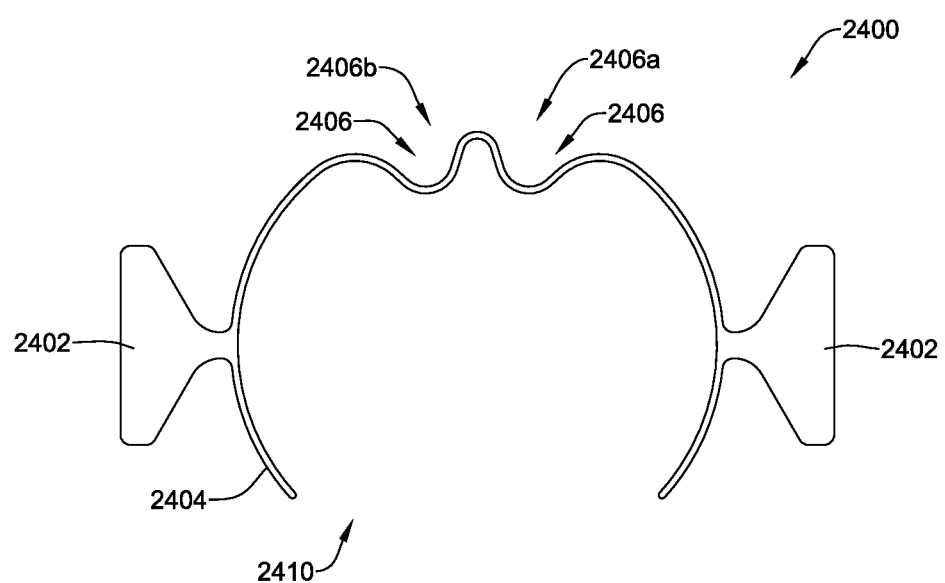
FIG. 24 is a schematic top view of an illustrative instrument clip.

FIG. 24 depicts a top view of a clip 2400, which may have a substantially similar configuration and function to the clip 1800. For example, the clip 2400 may include one or more two wings 2402, a clip body 2404, ports 2406, and an opening 2410, among other similar features. The clip 2400 may differ from the clip 1800 in that the clip 2400 may include a first port 2406a and a second port 2406b to facilitate securing two surgical tools or components between an outer surface of the clip 2400 and an inner surface of a tube of a surgical access tube assembly.

Figure 25:
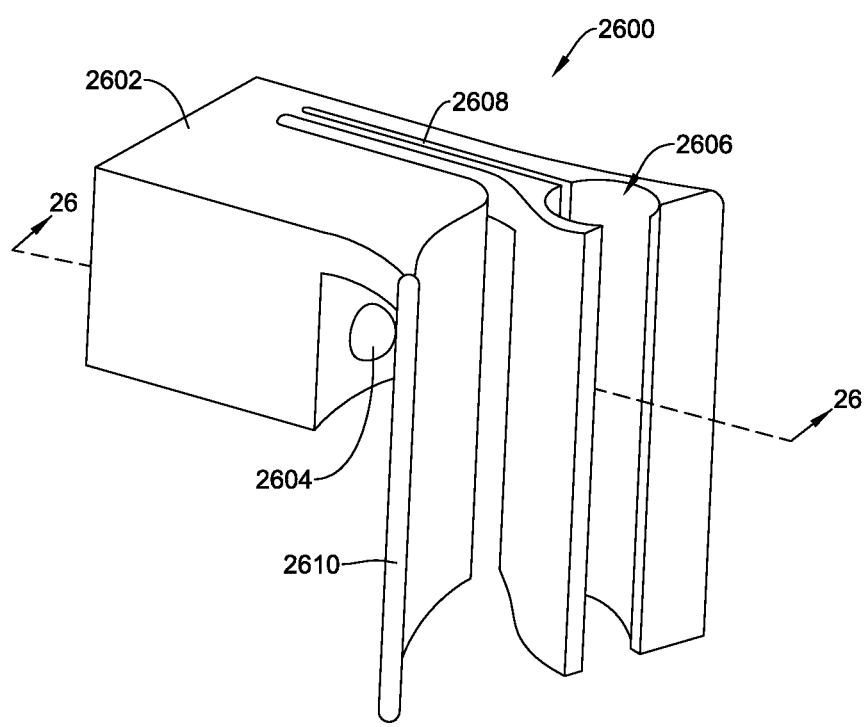
FIG. 25 is a schematic perspective view of an illustrative instrument clip.

FIG. 25 depicts a perspective view of an illustrative clip 2600 configured to secure to a surgical access tube assembly (e.g., the surgical access tube assemblies described herein or other suitable surgical access tube assemblies). The clip 2600 may include, among other suitable components, a housing 2602, a ball detent 2604, and a channel 2606 defined by the housing 2602.

In operation, the ball detent 2604 may be configured to engage an outside surface of a surgical access tube assembly, while an outside surface of the channel 2606 may be rounded so as to create a close-up abutment with an inside surface of the surgical access tube assembly. Further, a support 2610 having a rounded outside surface may also abut an inside surface of the surgical access tube assembly to improve stability of the clip 2600 when used with a surgical access tube assembly.

In one example, the channel 2606 may be configured to receive one or more instruments (e.g., a nerve root retractor, lights, etc.). In some cases, a slit 2608 may be connected to the channel 2606 to facilitate the channel 2606 expanding and receiving components having larger diameters than a natural diameter of the channel 2606 (e.g., a natural diameter may be a diameter of the channel 2606 without any forces acting on the channel 2606 by received components).

Figure 26:
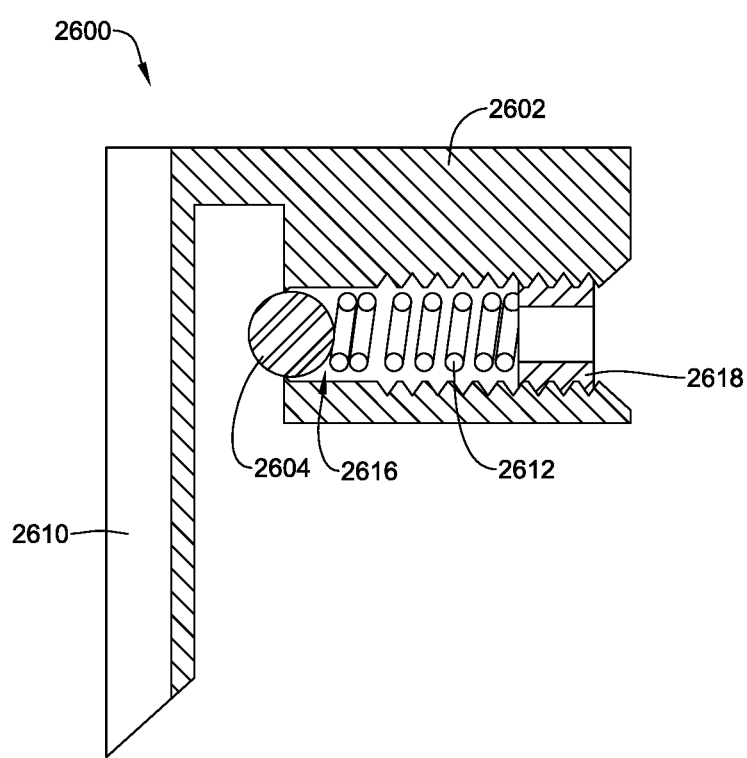
FIG. 26 is a schematic cross-sectional view of the instrument clip depicted in FIG. 25, taken along line 26-26.

FIG. 26 depicts a cross-sectional view of the clip 2600 taken along line 26-26 in FIG. 25. As depicted, the ball detent 2604 may be kept at a given location relative to the housing 2602 according to a resistance of a spring 2612. When the clip 2600 is attached to a surgical access tube assembly, the ball detent 2604 may engage an outer surface of the surgical access tube assembly and compress the spring 2612 and cause the ball detent 2604 to recede into a channel 2616. Further, in some cases, the clip 2600 may include a set screw 2618 within the channel 2616 (e.g., a threaded portion of the channel) to abut an end of the spring 2612 and ensure the ball detent 2604 cannot fully retracted into the channel 2616 unless intended to do so. The set screw 2618 may be adjusted to adjust an amount of force acting on the ball detent 2604. Although not depicted in the Figures, a surgical access tube assembly may include a channel or indent on an outside surface that may be configured to receive the ball detent 2604 in response to a force provided by the spring 2612 on the ball detent 2604 when clip 2600 engages the surgical access tube assembly.

Figure 27:
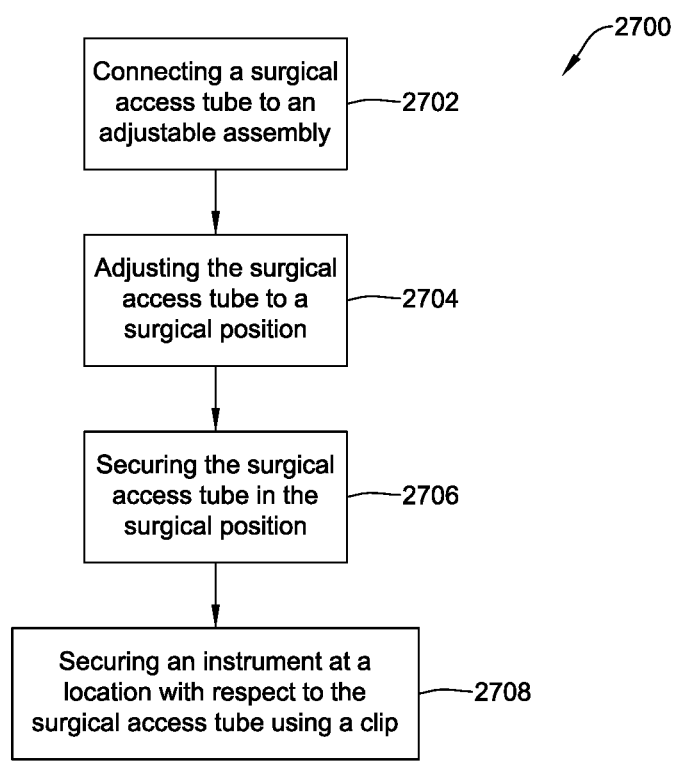
FIG. 27 is a schematic diagram of an illustrative method.

FIG. 27 depicts a method 2700 of positioning a surgical access tube assembly and an instrument at a surgical site. The method 2700 may include connecting 2702 a surgical access tube assembly 200 or other surgical access tube assembly discussed herein to an adjustment assembly 112 or other adjustment assembly discussed herein, where the adjustment assembly is connected to or may be connected to an articulating arm, such as an articulating surgical robot arm. The adjustment assembly 112 and the surgical access tube assembly 200 may connect in any suitable manner. In one example, an end of the surgical access tube assembly 200 may be inserted into a channel of a surgical device connector 116 (e.g., of or associated with the adjustment assembly 112), or other surgical device connector discussed herein, and clipped therein.

The adjustment assembly 112 or the connected surgical access tube assembly 200 (e.g., via the surgical device connector 116) may be adjusted 2704 in any suitable manner discussed herein to position the surgical access tube assembly 200 at a surgical position. In one example, a portion of the adjustment assembly 112 (e.g., an elongated assembly 120 or other adjustable portion of the adjustment assembly 112) may be adjusted at a first location and at a second location to position the surgical access tube assembly 200 at or in the surgical position. When the adjustment assembly 112 includes the elongated assembly 120, the elongated assembly 120 may be translated along an axis and rotated about one or more axis at a joint location (e.g., a first location) and the adjustment assembly 112 may be adjusted with respect to the surgical device connector 116 about an axis at a second location to position the surgical access tube assembly at the surgical position (e.g., via adjustment about two or more axes or other suitable adjustment). The adjusting 2704 can be performed while the articulating arm is locked. In some examples, the adjusting 2704 includes disposing a distal end of the tube assembly 200 into an incision formed in a patient. Other suitable configurations for adjusting the adjustment assembly are contemplated.

Once the surgical access tube assembly 200 is positioned in the surgical position, the surgical access tube assembly 200 may be secured 2706 in the surgical position. Although other configurations are contemplated, the surgical access tube assembly 200 may be secured in the surgical position by actuating the actuator 122 or other similar actuator discussed herein to a locked position such that the elongated assembly 120 may be secured relative to the articulating arm. Additionally or alternatively, the actuation of the actuator 122 to the locked position may cause the surgical device connector 116 to be fixed relative to the elongated assembly 120, as discussed herein. In some examples, the actuator 122 is the sole component for modifying the adjustability of the adjustment assembly 112.

Before, while, or after securing the surgical access tube assembly 200 in the surgical position, an instrument (e.g., a nerve retractor, light, camera, irrigator, suction device, etc.) may be secured 2708 at a location with respect to the surgical access tube assembly 200. In some cases, a clip 1800 or other clip discussed herein may be inserted into a tube of the surgical access tube assembly 200 to engage the instrument between an inner surface of a tube 204 or other tube discussed herein of the surgical access tube assembly 200 and an outer surface of the clip 1800. In some cases, an instrument may be inserted into the tube 204 of the surgical access tube assembly 200, a port 1806 of the clip 1800 may be aligned with the instrument, the clip 1800 may be inserted into the tube by squeezing on edges of the clip 1800 to reduce a diameter of the clip 1800, positioning the clip 1800 in the tube 204 of the surgical access device 200, and positioning the port 1806 around the instrument to secure the instrument at a location with respect to a surgical site and the surgical access tube assembly 200.

In some examples, after one or both of the securing steps 2706, 2708, one or more steps of a surgical procedure is performed through a tube of the tube assembly 200. The one or more steps can include one or more steps of a spinal procedure, such as a facetectomy, decompression, annulotomy, discectomy, insertion of an implant, other steps, or combinations thereof.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The above detailed description should be read with reference to the drawings in which similar elements in different drawings are numbered the similarly. The drawings, which are not necessarily to scale, depict illustrative embodiments and are not intended to limit the scope of the invention.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An assembly, comprising:
   a first connector configured to connect to a surgical articulating arm;
   a second connector configured to connect to a surgical tool;
   a joint assembly coupled to the first connector;
   an elongated assembly coupled to the second connector; and
   an actuator coupled to the joint assembly,
   wherein the joint assembly is configured to receive the elongated assembly;
   wherein the actuator is configured to adjust to fix the elongated assembly at a location with respect to the joint assembly and adjust to release the elongated assembly from the location; and
   wherein the elongated assembly is configured to adjust to fix the second connector at a position with respect to the elongated assembly and adjust to release the second connector from the position.

2. The assembly of claim 1, wherein the second connector comprises a channel configured to receive the surgical tool when connecting the surgical tool to the second connector.

3. The assembly of claim 1, wherein the elongated assembly is adjustable relative to the first connector.

4. The assembly of claim 1, wherein the joint assembly comprises a housing and a rotational joint configured to couple to the elongated assembly, wherein the rotational joint is configured to rotationally adjust within the housing.

5. The assembly of claim 4, wherein the rotational joint comprises a ball joint.

6. The assembly of claim 1, further comprising:
   wherein the actuator has a first position with respect to the joint assembly when the actuator has released the elongated assembly; and
   wherein the actuator has a second position with respect to the joint assembly when the actuator has fixed the elongated assembly with respect to the joint assembly.

7. The assembly of claim 6, further comprising:
   wherein the joint assembly comprises a housing and a rotatable joint configured to receive the elongated assembly and rotate relative to the housing; and
   wherein when the actuator is in the first position, the rotatable joint and the elongated assembly are configured to rotate about two or more axes.

8. The assembly of claim 7, wherein the actuator is configured to cause the rotatable joint to be compressively fixed relative to the housing when the actuator is in the second position.

9. The assembly of claim 7, wherein the actuator is configured to cause the elongated assembly to be compressively fixed relative to the housing when the actuator is in the second position.

10. An assembly, comprising:
    a first connector configured to connect to a surgical articulating arm;
    a second connector configured to connect to a surgical tool;
    a joint assembly coupled to the first connector;
    an elongated assembly coupled to the second connector; and
    an actuator coupled to the joint assembly;
    wherein the joint assembly is configured to receive the elongated assembly;
    wherein the actuator is configured to adjust to fix the elongated assembly at a location with respect to the joint assembly and adjust to release the elongated assembly from the location;
    wherein the joint assembly comprises a housing and a rotational joint configured to couple to the elongated assembly; and
    wherein the rotational joint is configurated to rotationally adjust within the housing.

11. The assembly of claim 10, wherein the second connector is configured to adjust relative to the elongated assembly.

12. The assembly of claim 10, wherein the elongated assembly is configured to adjust to fix the second connector at a position with respect to the elongated assembly and adjust to release the second connector from the position.

13. The assembly of claim 10, wherein the second connector comprises a channel configured to receive the surgical tool when connecting the surgical tool to the second connector.

14. The assembly of claim 10, wherein the elongated assembly is adjustable relative to the first connector.

15. The assembly of claim 10, wherein the rotational joint comprises a ball joint.

16. The assembly of claim 10, further comprising:
wherein the actuator has a first position with respect to the joint assembly when the actuator has released the elongated assembly;
wherein the actuator has a second position with respect to the joint assembly when the actuator has fixed the elongated assembly with respect to the joint assembly;
wherein the joint assembly comprises a housing and a rotatable joint configured to receive the elongated assembly and rotate relative to the housing; and
wherein when the actuator is in the first position, the rotatable joint and the elongated assembly are configured to rotate about two or more axes.

17. The assembly of claim 16, wherein the actuator is configured to cause the rotatable joint to be compressively fixed relative to the housing when the actuator is in the second position.

18. The assembly of claim 16, wherein the actuator is configured to cause the elongated assembly to be compressively fixed relative to the housing when the actuator is in the second position.

19. An assembly, comprising:
a first connector configured to connect to a surgical articulating arm;
a second connector configured to connect to a surgical tool;
a joint assembly coupled to the first connector;
an elongated assembly coupled to the second connector; and
an actuator coupled to the joint assembly,
wherein the joint assembly is configured to receive the elongated assembly;
wherein the actuator is configured to adjust to fix the elongated assembly at a location with respect to the joint assembly and adjust to release the elongated assembly from the location;
wherein the actuator has a first position with respect to the joint assembly in which the joint assembly is unlocked and the elongated assembly is translatable relative to the joint assembly;
wherein the actuator has a second position with respect to the joint assembly in which the elongated assembly is fixed with respect to the joint assembly;
wherein the joint assembly comprises a housing and a rotatable joint configured to receive the elongated assembly and rotate relative to the housing; and
wherein when the actuator is in the first position, the rotatable joint and the elongated assembly are configured to rotate about two or more axes.

* * * * *